(12) United States Patent
Graycar et al.

(10) Patent No.: US 7,250,281 B2
(45) Date of Patent: *Jul. 31, 2007

(54) SUBTILISIN VARIANTS

(75) Inventors: Thomas P. Graycar, Pacifica, CA (US); Richard R. Bott, Burlingame, CA (US); Lori J. Wilson, Millbrae, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/323,324

(22) Filed: Dec. 18, 2002

(65) Prior Publication Data

US 2004/0023353 A1 Feb. 5, 2004

Related U.S. Application Data

(63) Continuation of application No. 08/322,678, filed on Oct. 13, 1994, now Pat. No. 6,586,221, which is a continuation-in-part of application No. 08/137,240, filed on Oct. 14, 1993, now abandoned.

(51) Int. Cl.
*C12N 9/56* (2006.01)
*C12N 15/57* (2006.01)
*C12D 15/74* (2006.01)
*C11D 3/386* (2006.01)

(52) U.S. Cl. .............. 435/222; 435/69.1; 435/252.31; 435/320.1; 435/471; 536/23.2; 510/300

(58) Field of Classification Search ............... 435/220, 435/221, 222, 471, 252.3, 320.1; 536/23.2
See application file for complete search history.

(56) References Cited

U.S. PATENT DOCUMENTS

| | | | |
|---|---|---|---|
| 4,914,031 A | 4/1990 | Zukowski et al. | 435/222 |
| 4,990,452 A * | 2/1991 | Bryan et al. | 435/222 |
| 5,013,657 A | 5/1991 | Bryan et al. | 435/222 |
| 5,116,741 A * | 5/1992 | Bryan et al. | 435/87 |
| 5,155,033 A | 10/1992 | Estell et al. | 435/221 |
| 5,182,204 A | 1/1993 | Estell et al. | 435/222 |
| 5,185,258 A | 2/1993 | Caldwell et al. | 435/220 |
| 5,204,015 A | 4/1993 | Caldwell et al. | 510/392 |
| RE34,606 E | 5/1994 | Estell et al. | 510/392 |
| 5,324,653 A | 6/1994 | van Eekelen et al. | 435/221 |
| 5,336,611 A | 8/1994 | van Eekelen et al. | 435/221 |
| 5,397,705 A * | 3/1995 | Zukowski et al. | 435/222 |
| 5,665,587 A * | 9/1997 | Aaslyng et al. | 435/221 |
| 5,677,272 A * | 10/1997 | Ghosh et al. | 510/306 |
| 5,679,630 A * | 10/1997 | Baeck et al. | 510/305 |
| 6,312,936 B1 * | 11/2001 | Poulose et al. | 435/219 |
| 6,465,235 B1 * | 10/2002 | Bott et al. | 435/220 |
| 6,815,193 B2 * | 11/2004 | Poulose et al. | 435/220 |

FOREIGN PATENT DOCUMENTS

| | | |
|---|---|---|
| EP | 0 251 446 | 1/1988 |
| EP | 0 328 229 | 8/1989 |
| EP | 0 398 539 | 11/1990 |
| EP | 0 405 901 | 1/1991 |
| EP | 0 405 902 | 1/1991 |
| WO | WO88/08028 | 10/1988 |
| WO | WO89/06276 | 7/1989 |
| WO | WO89/06279 | 7/1989 |
| WO | WO89/09819 | 10/1989 |
| WO | WO91/00345 | 1/1991 |
| WO | WO91/06637 | 5/1991 |
| WO | WO92/08778 | 5/1992 |
| WO | WO92/11357 | 7/1992 |
| WO | WO92/21760 | 12/1992 |
| WO | WO94/02618 | 2/1994 |
| WO | WO94/23053 | 10/1994 |

OTHER PUBLICATIONS

Reeck, G.R. et al. (1987) Cell 50:667.
Lewin, R. (1987) Science 237:1570.
[Genest, M. et al. (1982) Int'l J Pept Prot.Res 19(4):420-431] Chemical Abstracts 96:322 Abstract No. 96:213252c.
Smith, E.L. et al (1968) J Biol Chem 243:2184-2191.
Kurihara, M. (1972) J Biol Chem 247(17): 5619-5631.
Bott, R. (1988) J Biol Chem 263(16):7895-7906.
Markland, F.S. and Smith, E.L. (1971) in The Enzyme, vol. 3,, pp. 561-608,Academic Press.
Svendsen, B. (1976) Carlsberg Res Comm 41:237-291.
Stauffer, D.C. et al. (1965) J Biol Chem 244:5333-5338.
Polgar, et al. (1981) Biochimica et Biophysica Acta 667:351-354.
Pantoliano, M.W. et al (1989) Biochem 28:7205-7213.
Graycar, T.P. et al. (1992) Altering the Proteolytic Activity of Subtilisin Through Protein Engineering in Annals of the New York Academy of Sciences:Enzyme Engineering XI, vol. 672, 71-79, Clark D.S. and Estell, D.A., eds, New York Academy of Sciences, New York.
Bott, R.R et al. (1992) Using Structural Comparison as a Guide in Protein Engineering in Annals of the New York Academy of Sciences:Enzyme Engineering XI, vol. 672, 10-19, Clark D.S. and Estell, D.A., eds, New York Academy of Sciences, New York.
Wells, J.A. et al. (1987) Proc Natl Acad Sci USA 84:1219-1223.
Siezen, R.J. et al. (1991) Protein Engineering 4(7):719-737.

* cited by examiner

Primary Examiner—Kathleen M. Kerr
Assistant Examiner—William W. Moore

(57) ABSTRACT

Novel carbonyl hydrolase variants derived from the DNA sequences of naturally-occurring or recombinant non-human carbonyl hydrolases are disclosed. The variant carbonyl hydrolases, in general, are obtained by in vitro modification of a precursor DNA sequence encoding the naturally-occurring or recombinant carbonyl hydrolase to generate the substitution of a plurality of amino acid residues in the amino acid sequence of a precursor carbonyl hydrolase. Such variant carbonyl hydrolases have properties which are different from those of the precursor hydrolase, such as altered proteolytic activity, altered stability, etc. The substituted amino acid residues correspond to positions +76 in combination with one or more of the following residues +99, +101, +103, +104, +107, +123, +27, +105, +109, +126, +128, +135, +156, +166, +195, +197, +204, +206, +210, +216, +217, +218, +222, +260, +265 and/or +274 in *Bacillus amyloliquefaciens* subtilisin.

2 Claims, 17 Drawing Sheets

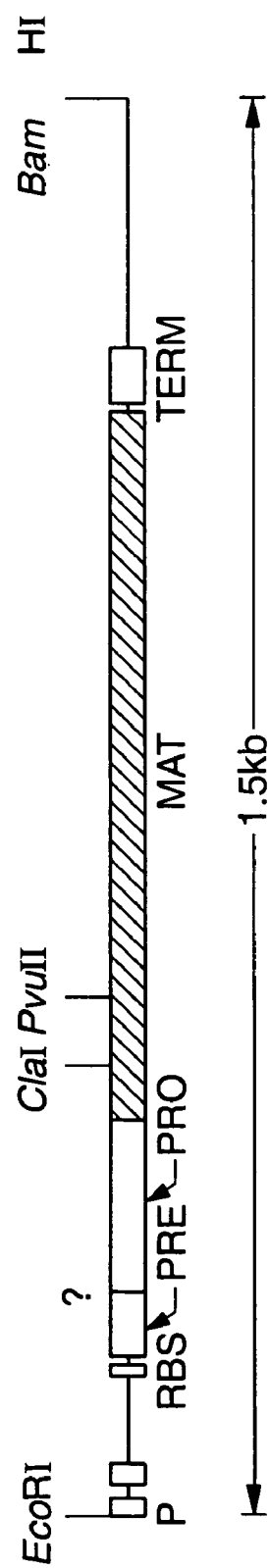
FIG._1A

FIG. 1B

```
                                                                                                                    -107
                                                                                                              RBS    Met
     GGTCTACTAAAATATTATTCCATACTATACAATTAATACACAGAATAATCTGTCTATTGGTTATTCTGCAAATGAAAAAAGGAGAGGATAAAGA GTG
     P                              3→                                      4→
              -80                      -100                              -90                              -60
     Arg Gly Lys Lys Val Trp Ile Ser Leu Leu Ala Leu Phe Thr Met Ala Phe Gly Ile Phe Thr Met Ser Thr Ser
 99  AGA GGC AAA AAA GTA TGG ATC AGT TTG CTG GCT TTA ACG ATG GCG TTC GGC ATC TTT ACG ATG AGC ACA TCC
                                            PRE                                                  -60
     Ser Ala Gln Ala Ala Gly Lys Lys Ser Asn Gly Glu Lys Lys Tyr Ile Val Gly Phe Lys Gln Thr Met Ser Thr Met
174  TCT GCC CAG GCA GCA GGG AAA AAG TCA AAC GGG GAA AAG AAA TAT ATT GTC GGG TTT AAA CAG ATG AGC ACA ATG
                                                            PRO                                        -40
     Ser Ala Ala Lys Lys Asp Val Ile Ser Glu Lys Gly Gly Lys Val Gln Lys Gln Phe Lys Tyr Val Asp Ala
249  AGC GCC GCT AAG AAG GAT GTC ATT TCT GAA AAA GGC GGG AAA GTG CAA AAG CAA TTC AAA TAT GTA GAC GCA
                                          -30                                                  -20
     Ala Ser Ala Thr Leu Asn Glu Lys Ala Val Lys Glu Leu Lys Lys Asp Pro Ser Val Ala Tyr Val Glu Glu Asp
324  GCT TCA GCT ACA TTA AAC GAA AAA GCT GTA AAA GAA TTG AAA AAA GAC CCG AGC GTC GCT TAC GTA GAA GAA GAT
                                      MAT                                          10
              -1         1
     His Val Ala His Ala Tyr Ala Gln Ser Val Pro Tyr Gly Val Ser Gln Ile Lys Ala Pro Ala Leu His Ser Gln
399  CAC GTA GCA CAT GCG TAC GCG CAG TCC GTG CCT TAC GGC GTA TCA CAA ATT AAA GCC CCT GCT CTG CAC TCT CAA
              20                                             30                              40
     Gly Tyr Thr Gly Ser Asn Val Lys Val Ala Val Ile Asp Ser Gly Ile Asp Ser Ser His Pro Asp Leu Lys Val
474  GGC TAC ACT GGA TCA AAT GTT AAA GTA GCG GTC ATC GAC AGC GGT ATC GAT TCT TCT CAT CCT GAT TTA AAG GTA
                                                            60                                  Asp
     Ala Gly Gly Ala Ser Met Val Pro Ser Glu Thr Asn Pro Phe Gln Asp Asn Asn Ser His Gly Thr His Val Ala
549  GCA GGC GGA GCC ATG GTT CCT TCT GAA ACA AAT CCT TTC CAA GAC AAC AAC TCT CAC GGA ACT CAC GTT GCC
              70                                    80                      Ser Ala 90
     Gly Thr Val Ala Ala Leu Asn Asn Ser Ile Gly Val Leu Gly Val Ala Pro Ser Ala Ser Leu Tyr Ala Val Lys
624  GGC ACA GTT GCG GCT CTT AAT AAC TCA ATC GGT GTT TTA GGC GTA GCA CCA AGC GCA TCA CTT TAC GCT GTA AAA
```

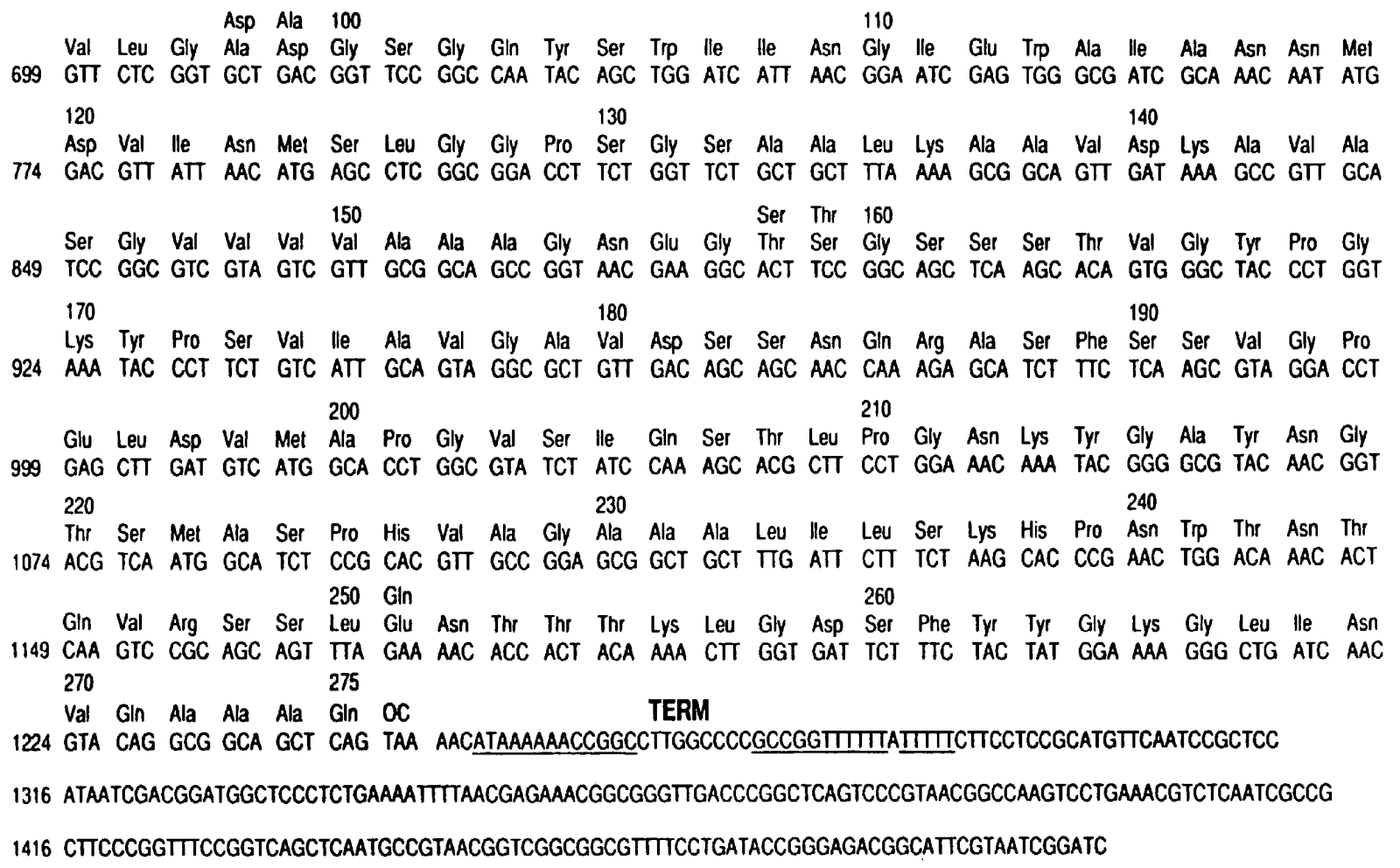

FIG._1C

Conserved Residues in Subtilisins from
*Bacillus Amyloliquefaciens*

COMPARISION OF SUBTILISIN SEQUENCES FROM:
B.amyloliquefaciens
B.subtilis
B.licheniformis
B.lentus

```
                     10                  20                  30
01  A Q S V P Y G V S Q I K A P A L H S Q G Y T G S N V K V A V I D S G I D S S H P
    A Q S V P Y G V S Q I K A P A L H S Q G Y T G S N V K V A V I D S G I D S S H P
    A Q T V P Y G I P L I K A D K V Q A Q G F K G A N V K V A V L D T G I Q A S H P
    A Q S V P W G I S R V Q A P A A H N R G L T G S G V K V A V L D T G I S T * H P 50                  60                  70
41  D L K V A G G A S M V P S E T N P P Q D N N S H G T H V A G T V A A L N N S I G
    D L N V R G G A S F V P S E T N P Y Q D G S S H G T H V A G T I A A L N N S I G
    D L N V V G G A S F V A G E A Y N * T D G N G H G T H V A G T V A A L D N T T G
    D L N I R G G A S F V P G E * P S T Q D G N G H G T H V A G T I A A L N N S I G 90                 100                 110
81  V L G V A P S A S L Y A V K V L G A D G S G Q Y S W I I N G I E W A I A N N M D
    V L G V A P S A S L Y A V K V L D S T G S G Q Y S W I I N G I E W A I S N N M D
    V L G V A P S V S L Y A V K V L N S S G S G S Y S G I V S G I E W A T T N G M D
    V L G V A P S A E L Y A V K V L G A S G S G S V S S I A Q G L E W A G N N G M H 130                 140                 150
121 V I N M S L G G P S G S A A L K A V D K A V A S G V V V V A A A G N E G T S G
    V I N M S L G G P T G S T A L K T V V D K A V S S G I V V A A A A G N E G S S G
    V I N M S L G G A S G S T A M K Q A V D N A Y A R G V V V V A A A G N S G N S G
    V A N L S L G S P S P S A T L E Q A V N S A T S R G V L V V A A S G N S G A G S
```

```
              170         180         190         200
161  S S T T V G Y P G K Y P S V I A V G A V D S S N Q R A S F S S V G P E L D V M A
     S T S T V G Y P A K Y P S T I H A V G A V N S S N R A S F S S V G A E L E V M A
     S T N T * * I G Y P A K Y D S V I A V G A V D S N S N R A S F S S Y G A G L D I V
     S T N T * * H S Y P A R Y A N A M A V G A T D Q N N R A S F S Q Y G A G L D I V A 210         220         230         240
201  P G V S I Q S T L P G N K Y G A Y N G T S M A S P H V A G A A A A L I L S K H P N
     P G V S I Q S T L P G G T Y G A Y N G T S M A T P H V A G A A A A L I L S K H P T
     P G A G V Q S T Y P T N Y A T L N G T S M A T P H V A G A A A A L I L H K H P N
     P G V N V Q S T Y P G S T Y A S L N G T S M A T P H V A G A A A A L V K Q K N P S 250         260         270
241  W T N T Q V R S S L E N T T T K L G D S F Y Y G K G L I N V Q A A A Q
     W T N A Q V R D R L E S T A T Y L G N S F Y Y G K G L I N V Q A A A Q
     L S A S Q V R N R L S S T A T Y L G S S F Y Y G K G L I N V E A A A Q
     W S N V Q I R N H L K N T A T S L G S T N L Y G S G L V N A E A A T R
```

FIG.—3B

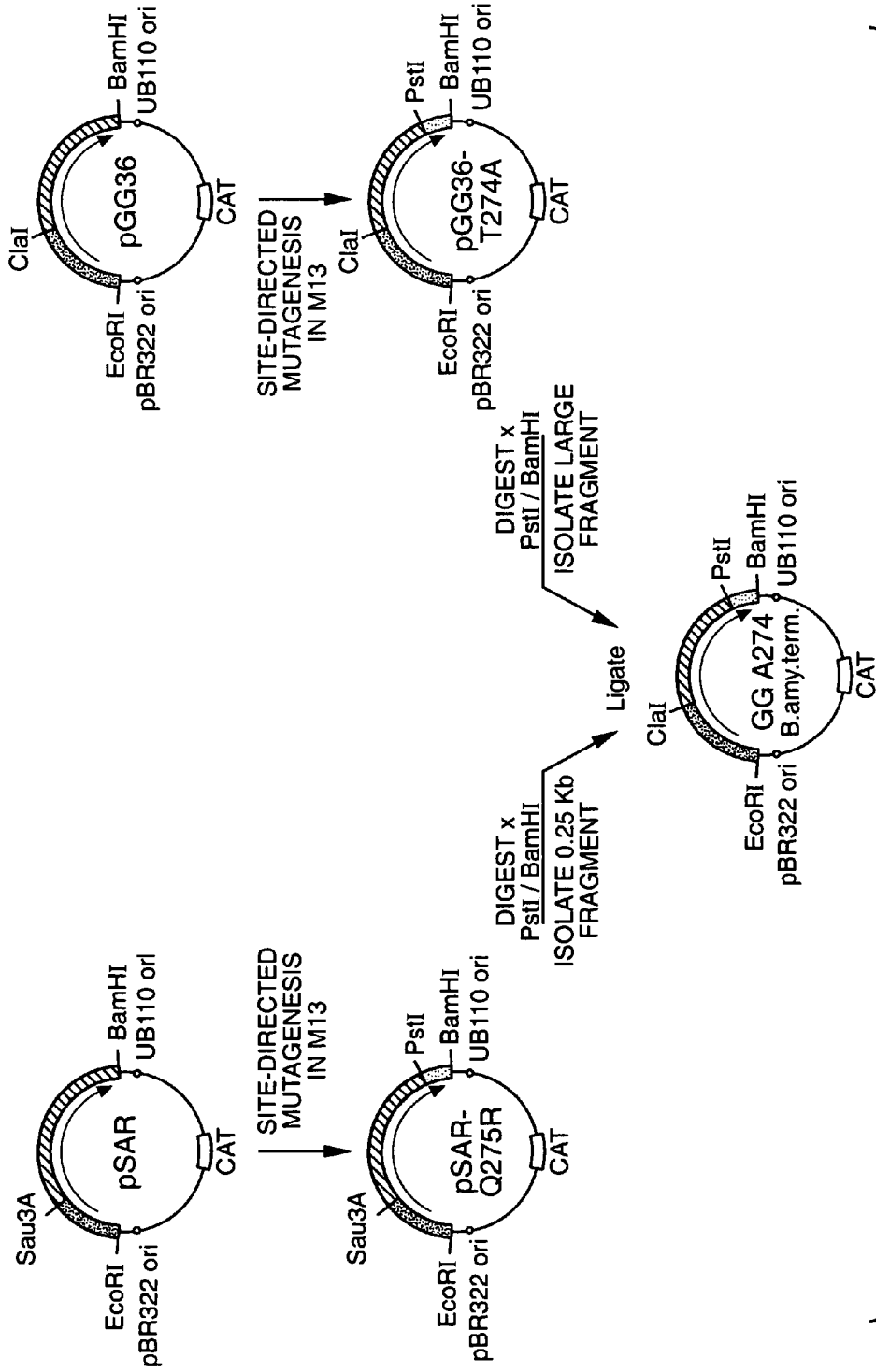

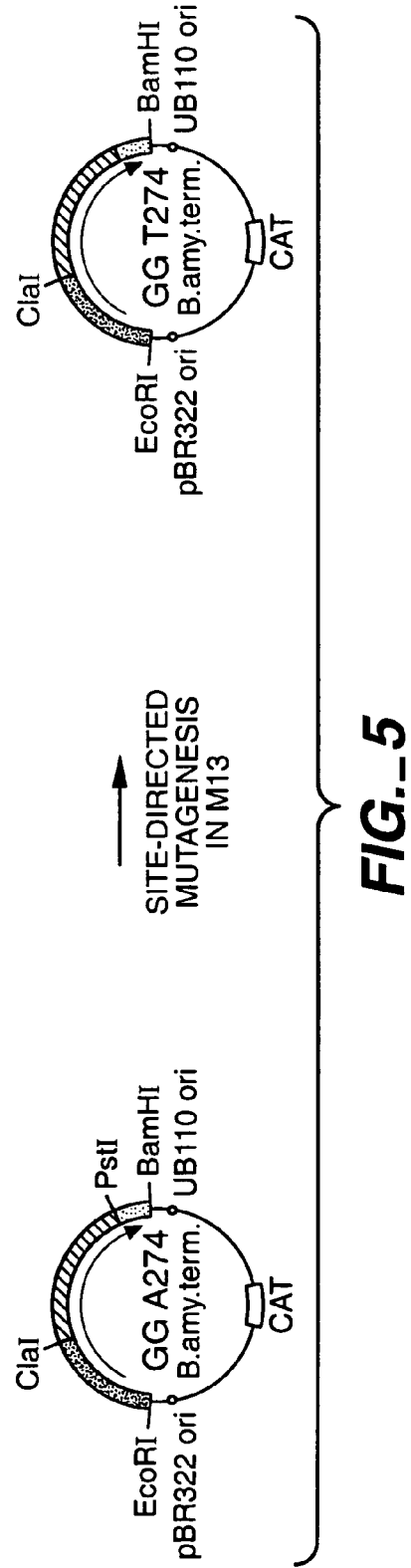
FIG._5

```
           10                  30                  50
ATGAAGAAACCGTTGGGGAAAATTGTCGCAAGCACCGCACTACTCATTTCTGTTGCTTTT
MetLysLysProLeuGlyLysIleValAlaSerThrAlaLeuLeuIleSerValAlaPhe 70                  90                  110
AGTTCATCGATCGCATCGGCTGCTGAAGAAGCAAAAGAAAAATATTTAATTGGCTTTAAT
SerSerSerIleAlaSerAlaAlaGluGluAlaLysGluLysTyrLeuIleGlyPheAsn 130                 150                 170
GAGCAGGAAGCTGTCAGTGAGTTTGTAGAACAAGTAGAGGCAAATGACGAGGTCGCCATT
GluGlnGluAlaValSerGluPheValGluGlnValGluAlaAsnAspGluValAlaIle 190                 210                 230
CTCTCTGAGGAAGAGGAAGTCGAAATTGAATTGCTTCATGAATTTGAAACGATTCCTGTT
LeuSerGluGluGluGluValGluIleGluLeuLeuHisGluPheGluThrIleProVal 250                 270                 290
TTATCCGTTGAGTTAAGCCCAGAAGATGTGGACGCGCTTGAACTCGATCCAGCGATTTCT
LeuSerValGluLeuSerProGluAspValAspAlaLeuGluLeuAspProAlaIleSer 310                 330                 350
TATATTGAAGAGGATGCAGAAGTAACGACAATGGCGCAATCAGTGCCATGGGGAATTAGC
TyrIleGluGluAspAlaGluValThrThrMetAlaGlnSerValProTrpGlyIleSer 370                 390                 410
CGTGTGCAAGCCCCAGCTGCCCATAACCGTGGATTGACAGGTTCTGGTGTAAAAGTTGCT
ArgValGlnAlaProAlaAlaHisAsnArgGlyLeuThrGlySerGlyValLysValAla 430                 450                 470
GTCCTCGATACAGGTATTTCCACTCATCCAGACTTAAATATTCGTGGTGGCGCTAGCTTT
ValLeuAspThrGlyIleSerThrHisProAspLeuAsnIleArgGlyGlyAlaSerPhe 490                 510                 530
GTACCAGGGGAACCATCCACTCAAGATGGGAATGGGCATGGCACGCATGTGGCCGGGACG
ValProGlyGluProSerThrGlnAspGlyAsnGlyHisGlyThrHisValAlaGlyThr 550                 570                 590
ATTGCTGCTTTAAACAATTCGATTGGCGTTCTTGGCGTAGCGCCGAGCGCGGAACTATAC
IleAlaAlaLeuAsnAsnSerIleGlyValLeuGlyValAlaProSerAlaGluLeuTyr
```

FIG._6A

```
              610                    630                    650
GCTGTTAAAGTATTAGGGGCGAGCGGTTCAGGTTCGGTCAGCTCGATTGCCCAAGGATTG
AlaValLysValLeuGlyAlaSerGlySerGlySerValSerSerIleAlaGlnGlyLeu 670                    690                    710
GAATGGGCAGGGAACAATGGCATGCACGTTGCTAATTTGAGTTTAGGAAGCCCTTCGCCA
GluTrpAlaGlyAsnAsnGlyMetHisValAlaAsnLeuSerLeuGlySerProSerPro 730                    750                    770
AGTGCCACACTTGAGCAAGCTGTTAATAGCGCGACTTCTAGAGGCGTTCTTGTTGTAGCG
SerAlaThrLeuGluGlnAlaValAsnSerAlaThrSerArgGlyValLeuValValAla 790                    810                    830
GCATCTGGGAATTCAGGTGCAGGCTCAATCAGCTATCCGGCCCGTTATGCGAACGCAATG
AlaSerGlyAsnSerGlyAlaGlySerIleSerTyrProAlaArgTyrAlaAsnAlaMet 850                    870                    890
GCAGTCGGAGCTACTGACCAAAACAACAACCGCGCCAGCTTTTCACAGTATGGCGCAGGG
AlaValGlyAlaThrAspGlnAsnAsnAsnArgAlaSerPheSerGlnTyrGlyAlaGly 910                    930                    950
CTTGACATTGTCGCACCAGGTGTAAACGTGCAGAGCACATACCCAGGTTCAACGTATGCC
LeuAspIleValAlaProGlyValAsnValGlnSerThrTyrProGlySerThrTyrAla 970                    990                    1010
AGCTTAAACGGTACATCGATGGCTACTCCTCATGTTGCAGGTGCAGCAGCCCTTGTTAAA
SerLeuAsnGlyThrSerMetAlaThrProHisValAlaGlyAlaAlaAlaLeuValLys 1030                   1050                   1070
CAAAAGAACCCATCTTGGTCCAATGTACAAATCCGCAATCATCTAAAGAATACGGCAACG
GlnLysAsnProSerTrpSerAsnValGlnIleArgAsnHisLeuLysAsnThrAlaThr 1090                   1110                   1130
AGCTTAGGAAGCACGAACTTGTATGGAAGCGGACTTGTCAATGCAGAAGCGGCAACACGC
SerLeuGlySerThrAsnLeuTyrGlySerGlyLeuValAsnAlaGluAlaAlaThrArg
```

FIG._6B

```
              10                  30                  50
ATGAAGAAACCGTTGGGGAAAATTGTCGCAAGCACCGCACTACTCATTTCTGTTGCTTTT
MetLysLysProLeuGlyLysIleValAlaSerThrAlaLeuLeuIleSerValAlaPhe 70                  90                 110
AGTTCATCGATCGCATCGGCTGCTGAAGAAGCAAAAGAAAAATATTTAATTGGCTTTAAT
SerSerSerIleAlaSerAlaAlaGluGluAlaLysGluLysTyrLeuIleGlyPheAsn 130                 150                 170
GAGCAGGAAGCTGTCAGTGAGTTTGTAGAACAAGTAGAGGCAAATGACGAGGTCGCCATT
GluGlnGluAlaValSerGluPheValGluGlnValGluAlaAsnAspGluValAlaIle 190                 210                 230
CTCTCTGAGGAAGAGGAAGTCGAAATTGAATTGCTTCATGAATTTGAAACGATTCCTGTT
LeuSerGluGluGluGluValGluIleGluLeuLeuHisGluPheGluThrIleProVal 250                 270                 290
TTATCCGTTGAGTTAAGCCCAGAAGATGTGGACGCGCTTGAACTCGATCCAGCGATTTCT
LeuSerValGluLeuSerProGluAspValAspAlaLeuGluLeuAspProAlaIleSer 310                 330                 350
TATATTGAAGAGGATGCAGAAGTAACGACAATGGCGCAATCAGTGCCATGGGGAATTAGC
TyrIleGluGluAspAlaGluValThrThrMetAlaGlnSerValProTrpGlyIleSer 370                 390                 410
CGTGTGCAAGCCCCAGCTGCCCATAACCGTGGATTGACAGGTTCTGGTGTAAAAGTTGCT
ArgValGlnAlaProAlaAlaHisAsnArgGlyLeuThrGlySerGlyValLysValAla 430                 450                 470
GTCCTCGATACAGGTATTTCCACTCATCCAGACTTAAATATTCGTGGTGGCGCTAGCTTT
ValLeuAspThrGlyIleSerThrHisProAspLeuAsnIleArgGlyGlyAlaSerPhe 490                 510                 530
GTACCAGGGGAACCATCCACTCAAGATGGGAATGGGCATGGCACGCATGTGGCCGGGACG
ValProGlyGluProSerThrGlnAspGlyAsnGlyHisGlyThrHisValAlaGlyThr 550                 570                 590
ATTGCTGCTTTAGACAACTCGATTGGCGTTCTTGGCGTAGCGCCGAGCGCGGAACTATAC
IleAlaAlaLeuAspAsnSerIleGlyValLeuGlyValAlaProSerAlaGluLeuTyr
```

FIG._7A

```
         610                   630                   650
GCTGTTAAAGTATTAGGGGCGAGCGGTTCAGGCGCCATCAGCTCGATTGCCCAAGGATTG
AlaValLysValLeuGlyAlaSerGlySerGlyAlaIleSerSerIleAlaGlnGlyLeu 670                   690                   710
GAATGGGCAGGGAACAATGGCATGCACGTTGCTAATTTGAGTTTAGGAAGCCCTTCGCCA
GluTrpAlaGlyAsnAsnGlyMetHisValAlaAsnLeuSerLeuGlySerProSerPro 730                   750                   770
AGTGCCACACTTGAGCAAGCTGTTAATAGCGCGACTTCTAGAGGCGTTCTTGTTGTAGCG
SerAlaThrLeuGluGlnAlaValAsnSerAlaThrSerArgGlyValLeuValValAla 790                   810                   830
GCATCTGGGAATTCAGGTGCAGGCTCAATCAGCTATCCGGCCCGTTATGCGAACGCAATG
AlaSerGlyAsnSerGlyAlaGlySerIleSerTyrProAlaArgTyrAlaAsnAlaMet 850                   870                   890
GCAGTCGGAGCTACTGACCAAAACAACAACCGCGCCAGCTTTTCACAGTATGGCGCAGGG
AlaValGlyAlaThrAspGlnAsnAsnAsnArgAlaSerPheSerGlnTyrGlyAlaGly 910                   930                   950
CTTGACATTGTCGCACCAGGTGTAAACGTGCAGAGCACATACCCAGGTTCAACGTATGCC
LeuAspIleValAlaProGlyValAsnValGlnSerThrTyrProGlySerThrTyrAla 970                   990                   1010
AGCTTAAACGGTACATCGATGGCTACTCCTCATGTTGCAGGTGCAGCAGCCCTTGTTAAA
SerLeuAsnGlyThrSerMetAlaThrProHisValAlaGlyAlaAlaAlaLeuValLys 1030                  1050                  1070
CAAAAGAACCCATCTTGGTCCAATGTACAAATCCGCAATCATCTAAAGAATACGGCAACG
GlnLysAsnProSerTrpSerAsnValGlnIleArgAsnHisLeuLysAsnThrAlaThr 1090                  1110                  1130
AGCTTAGGAAGCACGAACTTGTATGGAAGCGGACTTGTCAATGCAGAAGCGGCAACACGC
SerLeuGlySerThrAsnLeuTyrGlySerGlyLeuValAsnAlaGluAlaAlaThrArg
```

FIG._7B

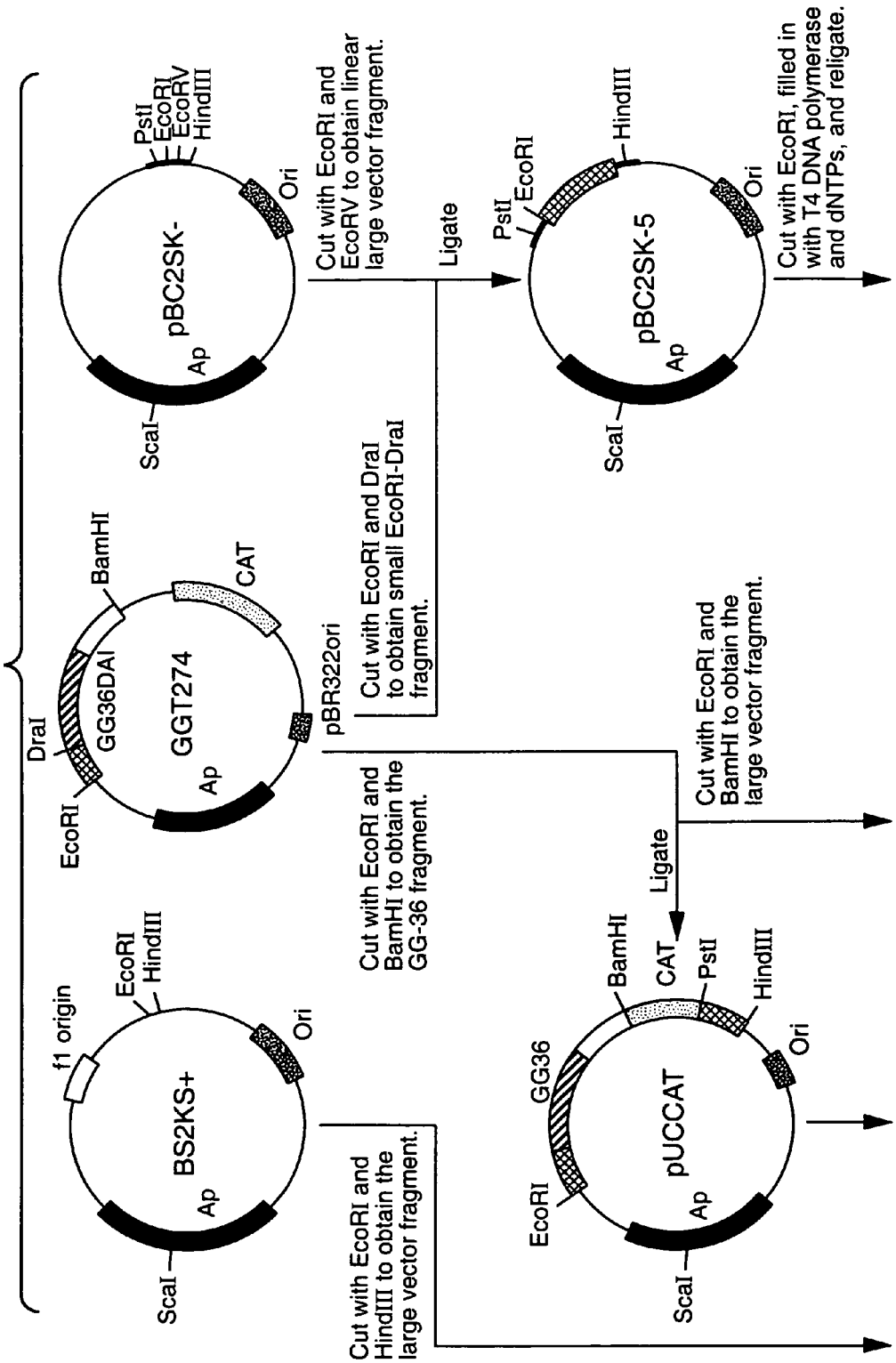
FIG._8A

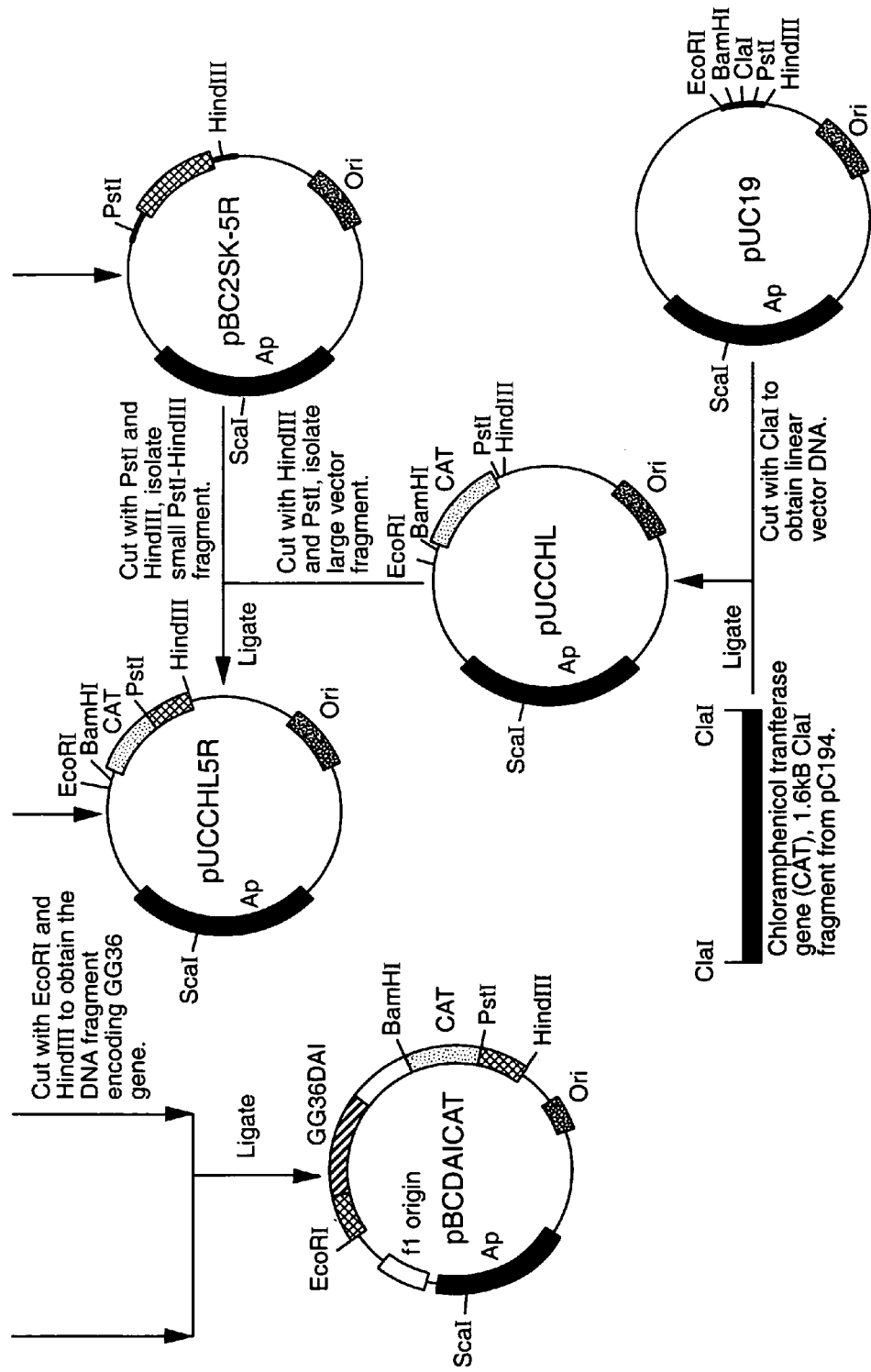
FIG._8B

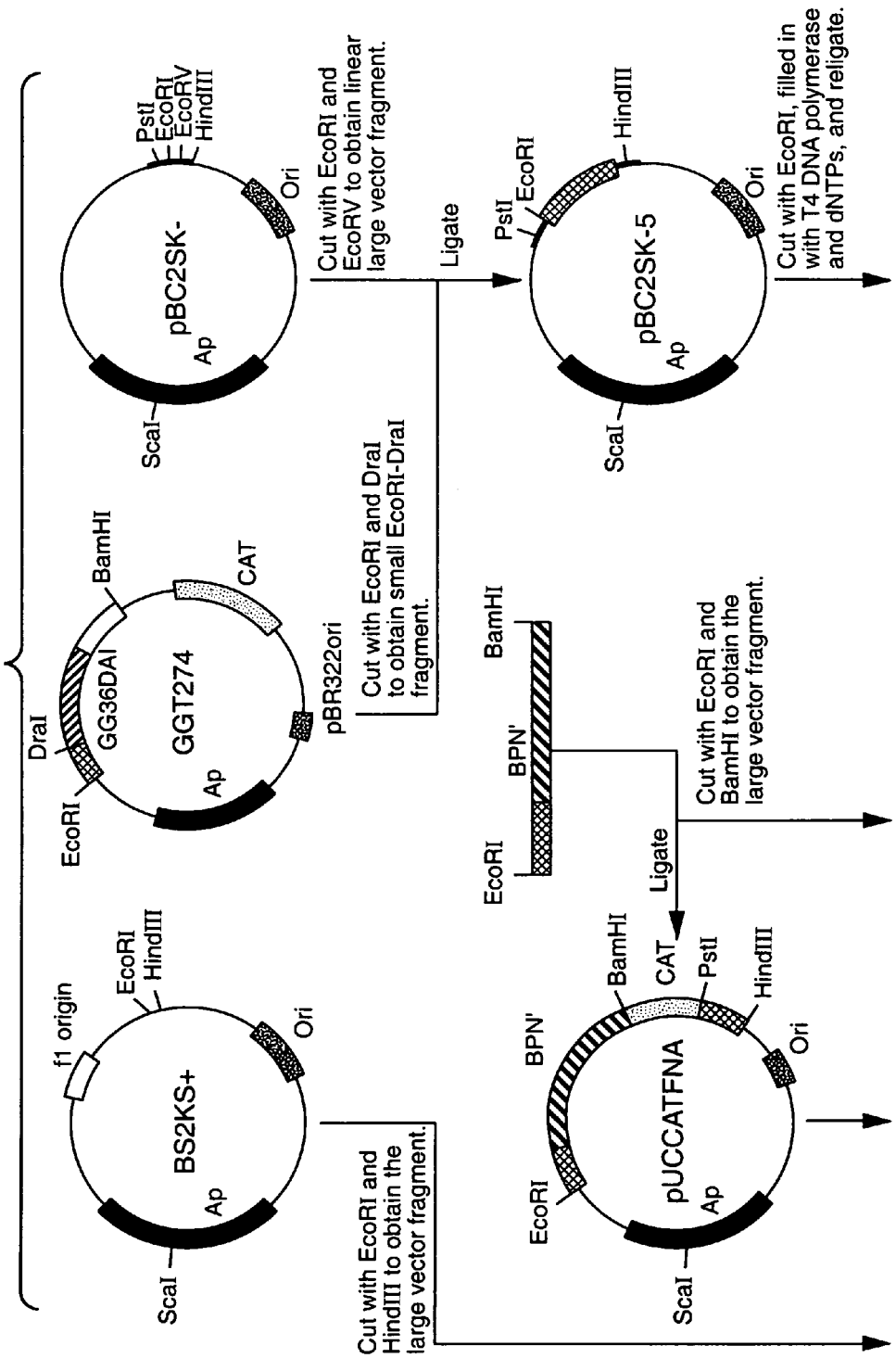
FIG._9A

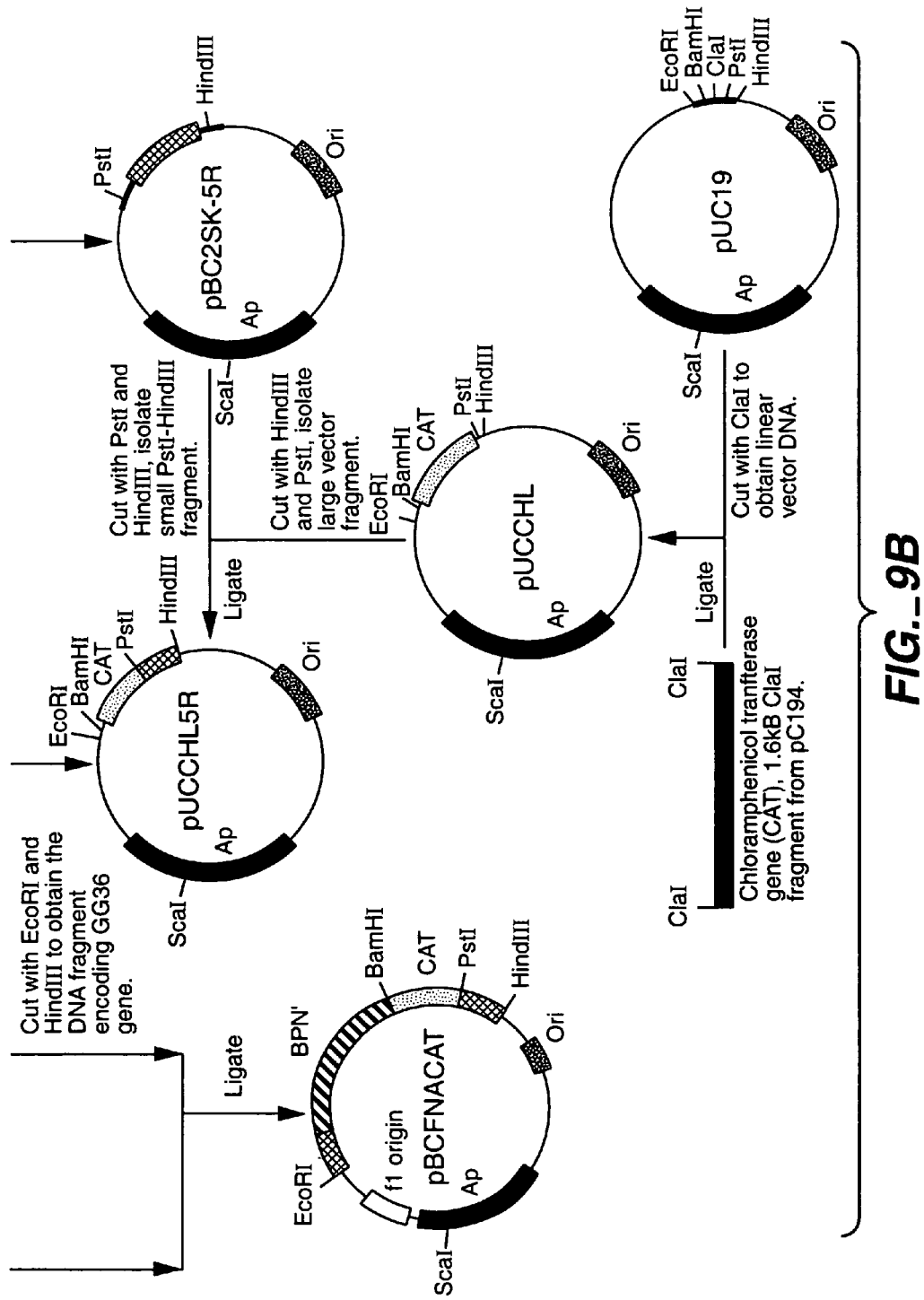
FIG._9B

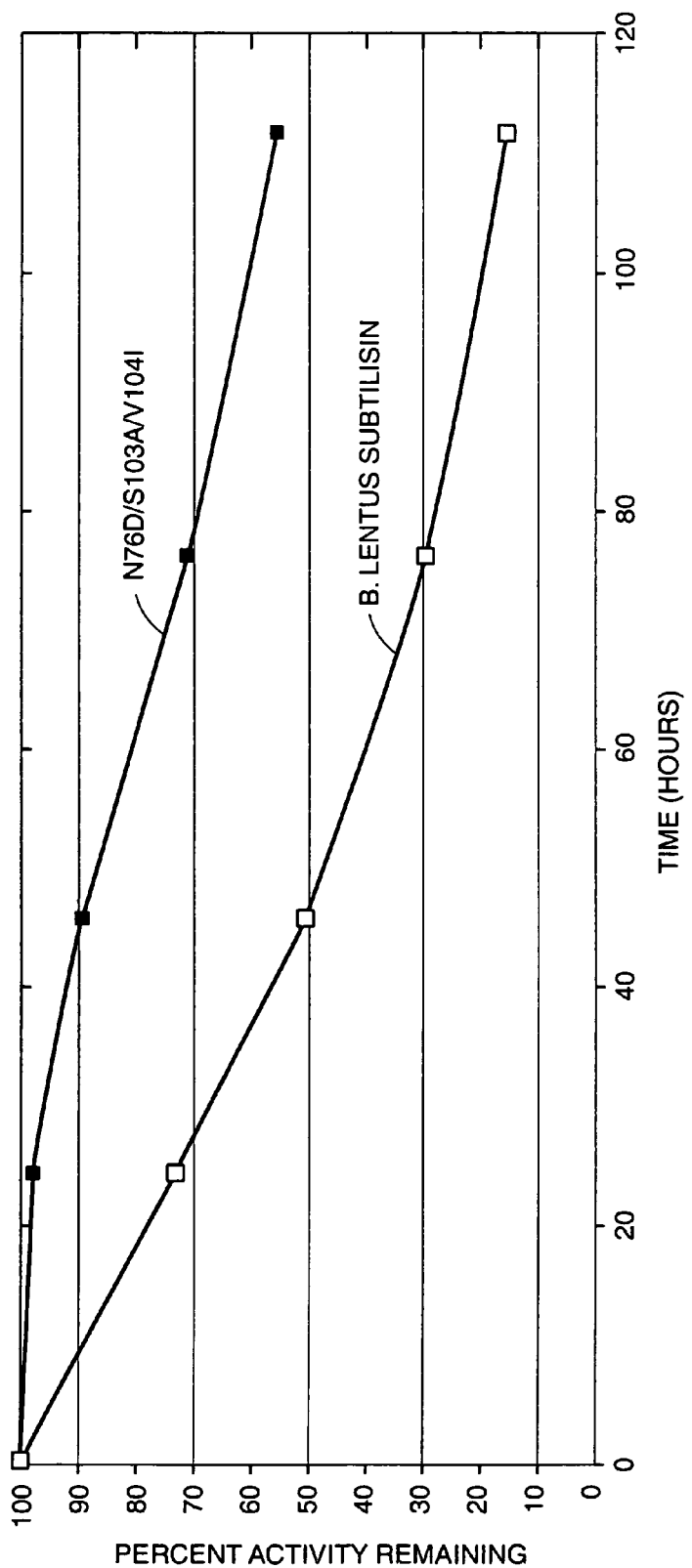
FIG._10

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

GAAGCTGCAA CTCGTTAAA              19

(2) INFORMATION FOR SEQ ID NO: 2:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 2:

GCTGCTCTAG ACAATTCG                                                    18

(2) INFORMATION FOR SEQ ID NO: 3:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 3:

GTATTAGGGG CGGACGGTCG AGGCGCCATC AGCTCGATT                              39

(2) INFORMATION FOR SEQ ID NO: 4:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 4:

TCAGGTTCGG TCTCGAGCGT TGCCCAAGGA TTG                                    33

(2) INFORMATION FOR SEQ ID NO: 5:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 5:

CACGTTGCTA GCTTGAGTTT AG                                                22

(2) INFORMATION FOR SEQ ID NO: 6:

(i) SEQUENCE CHARACTERISTICS:
            (A) LENGTH: 1497 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 6:

GGTCTACTAA AATATTATTC CATACTATAC AATTAATACA CAGAATAATC TGTCTATTGG       60

TTATTCTGCA AATGAAAAAA AGGAGAGGAT AAAGAGTGAG AGGCAAAAAA GTATGGATCA      120

GTTTGCTGTT TGCTTTAGCG TTAATCTTTA CGATGGCGTT CGGCAGCACA TCCTCTGCCC      180

AGGCGGCAGG GAAATCAAAC GGGGAAAAGA AATATATTGT CGGGTTTAAA CAGACAATGA      240

GCACGATGAG CGCCGCTAAG AAGAAAGATG TCATTTCTGA AAAAGGCGGG AAAGTGCAAA      300

AGCAATTCAA ATATGTAGAC GCAGCTTCAG TCACATTAAA CGAAAAAGCT GTAAAGAAT       360

TGAAAAAAGA CCCGAGCGTC GCTTACGTTG AAGAAGATCA CGTAGCACAT GCGTACGCGC      420

AGTCCGTGCC TTACGGCGTA TCACAAATTA AAGCCCCTGC TCTGCACTCT CAAGGCTACA      480

```
CTGGATCAAA TGTTAAAGTA GCGGTTATCG ACAGCGGTAT CGATTCTTCT CATCCTGATT    540

TAAAGGTAGC AAGCGGAGCC AGCATGGTTC CTTCTGAAAC AAATCCTTTC CAAGACAACA    600

ACTCTCACGG AACTCACGTT GCCGGCACAG TTGCGGCTCT TAATAACTCA ATCGGTGTAT    660

TAGGCGTTGC GCCAAGCGCA TCACTTTACG CTGTAAAAGT TCTCGGTGCT GACGGTTCCG    720

GCCAATACAG CTGGATCATT AACGGAATCG AGTGGGCGAT CGCAAACAAT ATGGACGTTA    780

TTAACATGAG CCTCGGCGGA CCTTCTGGTT CTGCTGCTTT AAAAGCGGCA GTTGATAAAG    840

CCGTTGCATC CGGCGTCGTA GTCGTTGCGG CAGCCGGTAA CGAAGGCACT TCCGGCAGCT    900

CAAGCACAGT GGGCTACCCT GGTAAATACC CTTCTGTCAT TGCAGTAGGC GCTGTTGACA    960

GCAGCAACCA AAGAGCATCT TTCTCAAGCG TAGGACCTGA GCTTGATGTC ATGGCACCTG   1020

GCGTATCTAT CCAAAGCACG CTTCCTGGAA ACAAATACGG GGCGTACAAC GGTACGTCAA   1080

TGGCATCTCC GCACGTTGCC GGAGCGGCTG CTTTGATTCT TTCTAAGCAC CCGAACTGGA   1140

CAAACACTCA AGTCCGCAGC AGTTTAGAAA ACACCACTAC AAAACTTGGT GATTCTTTGT   1200

ACTATGGAAA AGGGCTGATC AACGTACAAG CGGCAGCTCA GTAAAACATA AAAAACCGGC   1260

CTTGGCCCCG CCGGTTTTTT ATTATTTTTC TTCCTCCGCA TGTTCAATCC GCTCCATAAT   1320

CGACGGATGG CTCCCTCTGA AAATTTTAAC GAGAAACGGC GGGTTGACCC GGCTCAGTCC   1380

CGTAACGGCC AACTCCTGAA ACGTCTCAAT CGCCGCTTCC CGGTTTCCGG TCAGCTCAAT   1440

GCCATAACGG TCGGCGGCGT TTTCCTGATA CCGGGAGACG GCATTCGTAA TCGGATC     1497
```

(2) INFORMATION FOR SEQ ID NO: 7:

(i) SEQUENCE CHARACTERISTICS:
        (A) LENGTH: 275 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

```
Ala Gln Ser Val Pro Tyr Gly Val Ser Gln Ile Lys Ala Pro Ala Leu
1               5                  10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175
```

```
Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
        210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
            245                 250                 255

Leu Gly Asp Ser Phe Tyr Tyr Gly Lys Gly Leu Ile Asn Val Gln Ala
            260                 265                 270

Ala Ala Gln
        275

(2) INFORMATION FOR SEQ ID NO: 8:

(i) SEQUENCE CHARACTERISTICS:
        (A) LENGTH: 275 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
            35                  40                  45

Ser Phe Val Pro Ser Glu Thr Asn Pro Tyr Gln Asp Gly Ser Ser His
        50                  55                  60

Gly Thr His Val Ala Gly Thr Ile Ala Ala Leu Asn Asn Ser Ile Gly
65                  70                  75                  80

Val Leu Gly Val Ser Pro Ser Ala Ser Leu Tyr Ala Val Lys Val Leu
            85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
            115                 120                 125

Pro Thr Gly Ser Thr Ala Leu Lys Thr Val Val Asp Lys Ala Val Ser
        130                 135                 140

Ser Gly Ile Val Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
            165                 170                 175

Val Gly Ala Val Asn Ser Ser Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Gly Thr Tyr Gly Ala Tyr Asn Gly Thr Ser Met Ala Thr
        210                 215                 220

Pro His Val Ala Gly Ala Ala Leu Ile Leu Ser Lys His Pro Thr
225                 230                 235                 240
```

```
Trp Thr Asn Ala Gln Val Arg Asp Arg Leu Glu Ser Thr Ala Thr Tyr
            245                 250                 255

Leu Gly Asn Ser Phe Tyr Tyr Gly Lys Gly Leu Ile Asn Val Gln Ala
            260                 265                 270

Ala Ala Gln
        275

(2) INFORMATION FOR SEQ ID NO: 9:

(i) SEQUENCE CHARACTERISTICS:
        (A) LENGTH: 274 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
            35                  40                  45

Ser Phe Val Ala Gly Glu Ala Tyr Asn Thr Asp Gly Asn Gly His Gly
        50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
            115                 120                 125

Ser Gly Ser Thr Ala Met Lys Gln Ala Val Asp Asn Ala Tyr Ala Arg
            130                 135                 140

Gly Val Val Val Ala Ala Ala Gly Asn Ser Gly Asn Ser Gly Ser
145                 150                 155                 160

Thr Asn Thr Ile Gly Tyr Pro Ala Lys Tyr Asp Ser Val Ile Ala Val
            165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
            195                 200                 205

Pro Thr Asn Thr Tyr Ala Thr Leu Asn Gly Thr Ser Met Ala Ser Pro
            210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
            245                 250                 255

Gly Ser Ser Phe Tyr Tyr Gly Lys Gly Leu Ile Asn Val Glu Ala Ala
            260                 265                 270

Ala Gln
```

-continued (2) INFORMATION FOR SEQ ID NO: 10:

(i) SEQUENCE CHARACTERISTICS:
        (A) LENGTH: 269 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO: 11:

(i) SEQUENCE CHARACTERISTICS:
        (A) LENGTH: 1140 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

```
ATGAAGAAAC CGTTGGGGAA AATTGTCGCA AGCACCGCAC TACTCATTTC TGTTGCTTTT      60

AGTTCATCGA TCGCATCGGC TGCTGAAGAA GCAAAAGAAA AATATTTAAT TGGCTTTAAT     120
```

```
GAGCAGGAAG CTGTCAGTGA GTTTGTAGAA CAAGTAGAGG CAAATGACGA GGTCGCCATT    180

CTCTCTGAGG AAGAGGAAGT CGAAATTGAA TTGCTTCATG AATTTGAAAC GATTCCTGTT    240

TTATCCGTTG AGTTAAGCCC AGAAGATGTG GACGCGCTTG AACTCGATCC AGCGATTTCT    300

TATATTGAAG AGGATGCAGA AGTAACGACA ATGGCGCAAT CAGTGCCATG GGGAATTAGC    360

CGTGTGCAAG CCCCAGCTGC CCATAACCGT GGATTGACAG GTTCTGGTGT AAAAGTTGCT    420

GTCCTCGATA CAGGTATTTC CACTCATCCA GACTTAAATA TTCGTGGTGG CGCTAGCTTT    480

GTACCAGGGG AACCATCCAC TCAAGATGGG AATGGGCATG GCACGCATGT GGCCGGGACG    540

ATTGCTGCTT TAAACAATTC GATTGGCGTT CTTGGCGTAG CGCCGAGCGC GGAACTATAC    600

GCTGTTAAAG TATTAGGGGC GAGCGGTTCA GGTTCGGTCA GCTCGATTGC CCAAGGATTG    660

GAATGGGCAG GGAACAATGG CATGCACGTT GCTAATTTGA GTTTAGGAAG CCCTTCGCCA    720

AGTGCCACAC TTGAGCAAGC TGTTAATAGC GCGACTTCTA GAGGCGTTCT TGTTGTAGCG    780

GCATCTGGGA ATTCAGGTGC AGGCTCAATC AGCTATCCGG CCCGTTATGC GAACGCAATG    840

GCAGTCGGAG CTACTGACCA AAACAACAAC CGCGCCAGCT TTTCACAGTA TGGCGCAGGG    900

CTTGACATTG TCGCACCAGG TGTAAACGTG CAGAGCACAT ACCCAGGTTC AACGTATGCC    960

AGCTTAAACG GTACATCGAT GGCTACTCCT CATGTTGCAG GTGCAGCAGC CCTTGTTAAA   1020

CAAAAGAACC CATCTTGGTC CAATGTACAA ATCCGCAATC ATCTAAAGAA TACGGCAACG   1080

AGCTTAGGAA GCACGAACTT GTATGGAAGC GGACTTGTCA ATGCAGAAGC GGCAACACGC   1140
```

(2) INFORMATION FOR SEQ ID NO: 12:

(i) SEQUENCE CHARACTERISTICS:
        (A) LENGTH: 1140 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

```
ATGAAGAAAC CGTTGGGGAA AATTGTCGCA AGCACCGCAC TACTCATTTC TGTTGCTTTT     60

AGTTCATCGA TCGCATCGGC TGCTGAAGAA GCAAAAGAAA AATATTTAAT TGGCTTTAAT    120

GAGCAGGAAG CTGTCAGTGA GTTTGTAGAA CAAGTAGAGG CAAATGACGA GGTCGCCATT    180

CTCTCTGAGG AAGAGGAAGT CGAAATTGAA TTGCTTCATG AATTTGAAAC GATTCCTGTT    240

TTATCCGTTG AGTTAAGCCC AGAAGATGTG GACGCGCTTG AACTCGATCC AGCGATTTCT    300

TATATTGAAG AGGATGCAGA AGTAACGACA ATGGCGCAAT CAGTGCCATG GGGAATTAGC    360

CGTGTGCAAG CCCCAGCTGC CCATAACCGT GGATTGACAG GTTCTGGTGT AAAAGTTGCT    420

GTCCTCGATA CAGGTATTTC CACTCATCCA GACTTAAATA TTCGTGGTGG CGCTAGCTTT    480

GTACCAGGGG AACCATCCAC TCAAGATGGG AATGGGCATG GCACGCATGT GGCCGGGACG    540

ATTGCTGCTT TAGACAACTC GATTGGCGTT CTTGGCGTAG CGCCGAGCGC GGAACTATAC    600

GCTGTTAAAG TATTAGGGGC GAGCGGTTCA GGCGCCATCA GCTCGATTGC CCAAGGATTG    660

GAATGGGCAG GGAACAATGG CATGCACGTT GCTAATTTGA GTTTAGGAAG CCCTTCGCCA    720

AGTGCCACAC TTGAGCAAGC TGTTAATAGC GCGACTTCTA GAGGCGTTCT TGTTGTAGCG    780

GCATCTGGGA ATTCAGGTGC AGGCTCAATC AGCTATCCGG CCCGTTATGC GAACGCAATG    840

GCAGTCGGAG CTACTGACCA AAACAACAAC CGCGCCAGCT TTTCACAGTA TGGCGCAGGG    900

CTTGACATTG TCGCACCAGG TGTAAACGTG CAGAGCACAT ACCCAGGTTC AACGTATGCC    960
```

-continued

```
AGCTTAAACG GTACATCGAT GGCTACTCCT CATGTTGCAG GTGCAGCAGC CCTTGTTAAA      1020

CAAAAGAACC CATCTTGGTC CAATGTACAA ATCCGCAATC ATCTAAAGAA TACGGCAACG      1080

AGCTTAGGAA GCACGAACTT GTATGGAAGC GGACTTGTCA ATGCAGAAGC GGCAACACGC      1140
```

(2) INFORMATION FOR SEQ ID NO: 13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

```
TATGCCAGCC ACAACGGTAC TTCGATGGCT                                        30
```

(2) INFORMATION FOR SEQ ID NO: 14:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

```
CACAGTTGCG GCTCTAGATA ACTCAATCGG T                                      31
```

(2) INFORMATION FOR SEQ ID NO: 15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

```
GCTGACGGTT CCGGCGCTAT TAGTTGGATC ATT                                    33
```

SUBTILISIN VARIANTS

CROSS-REFERENCE TO RELATED APPLICATIONS

The present application is a Continuation of U.S. patent application Ser. No. 08/322,678, filed Oct. 13, 1994, now U.S. Pat. No. 6,586,221, issued Jul. 1, 2003, which is a Continuation-in-Part of U.S. patent application Ser. No. 08/137,240, filed Oct. 14, 1993, now abandoned.

FIELD OF THE INVENTION

The present invention relates to novel carbonyl hydrolase variants having an amino acid sequence wherein a plurality of amino acid residues of a precursor carbonyl hydrolase, specifically those at positions corresponding or equivalent to residue +76 in combination with one or more of the residues selected from the group consisting of +99, +101, +103, +104, +107, +123, +27, +105, +109, +126, +128, +135, +156, +166, +195, +197, +204, +206, +210, +216, +217, +218, +222, +260, +265 and/or +274 in *Bacillus amyloliquefaciens* subtilisin, have been substituted with a different amino acid. Such mutant/variant carbonyl hydrolases, in general, are obtained by in vitro modification of a precursor DNA sequence encoding a naturally-occurring or recombinant carbonyl hydrolase to encode the substitution of a plurality of these amino acid residues in a precursor amino acid sequence alone or in combination with other substitution, insertion or deletion in the precursor amino acid sequence.

BACKGROUND OF THE INVENTION

Serine proteases are a subgroup of carbonyl hydrolase. They comprise a diverse class of enzymes having a wide range of specificities and biological functions. Stroud, R. *Sci. Amer.*, 131:74–88. Despite their functional diversity, the catalytic machinery of serine proteases has been approached by at least two genetically distinct families of enzymes: the subtilisins and the mammalian chymotrypsin related and homologous bacterial serine proteases (e.g., trypsin and *S. gresius* trypsin). These two families of serine proteases show remarkably similar mechanisms of catalysis. Kraut, J. (1977), *Ann. Rev. Biochem.*, 46:331–358. Furthermore, although the primary structure is unrelated, the tertiary structure of these two enzyme families bring together a conserved catalytic triad of amino acids consisting of serine, histidine and aspartate.

Subtilisin is a serine endoprotease (MW 27,500) which is secreted in large amounts from a wide variety of Bacillus species and other microorganisms. The protein sequence of subtilisin has been determined from at least four different species of Bacillus. Markland, F. S., et al. (1983), *Hoppe-Seyler's Z. Physiol. Chem.*, 364:1537–1540. The three-dimensional crystallographic structure of *Bacillus amyloliquefaciens* subtilisin to 2.5 Å resolution has also been reported. Wright, C. S., et al. (1969), *Nature*, 221:235–242; Drenth, J., et al. (1972), *Eur. J. Biochem.*, 26:177–181. These studies indicate that although subtilisin is genetically unrelated to the mammalian serine proteases, it has a similar active site structure. The x-ray crystal structures of subtilisin containing covalently bound peptide inhibitors (Robertus, J. D., et al. (1972), *Biochemistry*, 11:2439–2449) or product complexes (Robertus, J. D., et al. (1976), *J. Biol. Chem.*, 251:1097–1103) have also provided information regarding the active site and putative substrate binding cleft of subtilisin. In addition, a large number of kinetic and chemical modification studies have been reported for subtilisin (Philipp, M., et al. (1983), *Mol. Cell. Biochem.*, 51:5–32; Svendsen, B. (1976), *Carlsberg Res. Comm.*, 41:237–291; Markland, F. S. Id.) as well as at least one report wherein the side chain of methionine at residue 222 of subtilisin was converted by hydrogen peroxide to methionine-sulfoxide (Stauffer, D. C., et al. (1965), *J. Biol. Chem.*, 244:5333–5338) and the side chain of serine at residue 221 converted to cysteine by chemical modification (Polgar, et al. (1981), *Biochimica et Biophysica Acta*, 667:351–354.)

U.S. Pat. No. 4,760,025 (RE 34,606) discloses the modification of subtilisin amino acid residues corresponding to positions in *Bacillus amyloliquefaciens* subtilisin tyrosine −1, aspartate +32, asparagine +155, tyrosine +104, methionine +222, glycine +166, histidine +64, glycine +169, phenylalanine +189, serine +33, serine +221, tyrosine +217, glutamate +156 and alanine +152. U.S. Pat. No. 5,182,204 discloses the modification of the amino acid +224 residue in *Bacillus amyloliquefaciens* subtilisin and equivalent positions in other subtilisins which may be modified by way of substitution, insertion or deletion and which may be combined with modifications to the residues identified in U.S. Pat. No. 4,760,025 (RE 34,606) to form useful subtilisin mutants or variants. U.S. Pat. No. 5,155,033 discloses similar mutant subtilisins having a modification at an equivalent position to +225 of *B. amyloliquefaciens* subtilisin. U.S. Pat. Nos. 5,185,258 and 5,204,015 disclose mutant subtilisins having a modification at positions +123 and/or +274. The disclosure of these patents is incorporated herein by reference, as is the disclosure of U.S. patent application Ser. No. 07/898,382, which discloses the modification of many amino acid residues within subtilisin, including specifically +99, +101, +103, +107, +126, +128, +135, +197 and +204. All of these patent /applications are commonly owned. U.S. Pat. No. 4,914,031 discloses certain subtilisin analogs, including a subtilisin modified at position +76. The disclosure of this patent is also incorporated herein by reference. The particular residues identified herein and/or the specific combinations claimed herein, however, are not identified in these references.

Accordingly, it is an object herein to provide carbonyl hydrolase (preferably subtilisin) variants containing the substitution of a plurality of amino acid residues in the DNA encoding a precursor carbonyl hydrolase corresponding to positions +76 in combination with one or more positions selected from the group +99, +101, +103, +104, +107, +123, +27, +105, +109, +126, +128, +135, +156, +166, +195, +197, +204, +206, +210, +216, +217, +218, +222, +260, +265 and/or +274 in *Bacillus amyloliquefaciens* subtilisin. Such variants generally have at least one property which is different from the same property of the carbonyl hydrolase precursor from which the amino acid sequence of said variant is derived.

It is a further object to provide DNA sequences encoding such carbonyl hydrolase variants, as well as expression vectors containing such variant DNA sequences.

Still further, another object of the invention is to provide host cells transformed with such vectors, as well as host cells which are capable of expressing such DNA to produce carbonyl hydrolase variants either intracellularly or extracellularly.

The references discussed above are provided solely for their disclosure prior to the filing date of the instant case, and nothing herein is to be construed as an admission that the

SUMMARY OF THE INVENTION

The invention includes non-naturally-occurring carbonyl hydrolase variants having a different proteolytic activity, stability, substrate specificity, pH profile and/or performance characteristic as compared to the precursor carbonyl hydrolase from which the amino acid sequence of the variant is derived. The precursor carbonyl hydrolase may be a naturally-occurring carbonyl hydrolase or recombinant hydrolase. Specifically, such carbonyl hydrolase variants have an amino acid sequence not found in nature, which is derived by replacement of a plurality of amino acid residues of a precursor carbonyl hydrolase with different amino acids. The plurality of amino acid residues of the precursor enzyme correspond to position +76 in combination with one or more of the following residues +99, +101, +103, +104, +107, +123, +27, +105,+109, +126, +128, +135, +156, +166, +195, +197, +204, +206, +210, +216, +217, +218, +222, +260, +265 and/or +274, where the numbered position corresponds to naturally-occurring subtilisin from *Bacillus amyloliquefaciens* or to equivalent amino acid residues in other carbonyl hydrolases or subtilisins, such as *Bacillus lentus* subtilisin. The carbonyl hydrolase variants of the present invention comprise replacement of amino acid residue +76 in combination with one or more additional modifications. Preferably the variant enzymes of the present invention comprise the substitution, deletion or insertion of amino acid residues in the following combinations: 76/99; 76/101; 76/103; 76/104; 76/107; 76/123; 76/99/101; 76/99/103; 76/99/104; 76/101/103; 76/101/104; 76/103/104; 76/104/107; 76/104/123; 76/107/123; 76/99/101/103; 76/99/101/104; 76/99/103/104; 76/101/103/104; 76/103/104/123; 76/104/107/123; 76/99/101/103/104; 76/99/103/104/123; 76/99/101/103/104/123; 76/103/104/128; 76/103/104/260; 76/103/104/265; 76/103/104/197; 76/103/104/105; 76/103/104/135; 76/103/104/126; 76/103/104/107; 76/103/104/210; 76/103/104/126/265 and/or 76/103/104/222. Most preferably the variant enzymes of the present invention comprise the substitution, deletion or insertion of an amino acid residue in the following combination of residues: 76/99; 76/104; 76/99/104; 76/103/104; 76/104/107; 76/101/103/104; 76/99/101/103/104 and 76/101/104 of *B. amyloliquefaciens* subtilisin.

The invention also includes variant DNA sequences encoding such carbonyl hydrolase or subtilisin variants. These variant DNA sequences are derived from a precursor DNA sequence which encodes a naturally-occurring or recombinant precursor enzyme. The variant DNA sequences are derived by modifying the precursor DNA sequence to encode the substitution of one or more specific amino acid residues encoded by the precursor DNA sequence corresponding to positions 76, 99, 101, 103, 104, 107, 123, 27, 105, 109, 126, 128, 135, 156, 166, 195, 197, 204, 206, 210, 216, 217, 218, 222, 260, 265 and/or 274 in *Bacillus amyloliquefaciens* or any combination thereof. Although the amino acid residues identified for modification herein are identified according to the numbering applicable to *B. amyloliquefaciens* (which has become the conventional method for identifying residue positions in all subtilisins), the preferred precursor DNA sequence useful in the present invention is the DNA sequence of *Bacillus lentus* as shown in FIG. 6 (Seq ID No.11).

The variant DNA sequences of the present invention encode the insertion or substitution of the amino acid residue 76 in combination with one or more additional modification. Preferably the variant DNA sequences encode the substitution or insertion of amino acid residues in the following combinations: 76/99; 76/101; 76/103; 76/104; 76/107; 76/123; 76/99/101; 76/99/103; 76/99/104; 76/101/103; 76/101/104; 76/103/104; 76/104/107; 76/104/123; 76/107/123; 76/99/101/103; 76/99/101/104; 76/99/103/104; 76/101/103/104; 76/103/104/123; 76/104/107/123; 76/99/101/103/104; 76/99/103/104/123; 76/99/101/103/104/123; 76/103/104/128; 76/103/104/260; 76/103/104/265; 76/103/104/197; 76/103/104/105; 76/103/104/135; 76/103/104/126; 76/103/104/107; 76/103/104/210; 76/103/104/126/265 and/or 76/103/104/222. Most preferably the variant DNA sequences encode for the modification of the following combinations of residues: 76/99; 76/104; 76/99/104; 76/103/104; 76/104/107; 76/101/103/104; 76/99/101/103/104 and 76/101/104. These recombinant DNA sequences encode carbonyl hydrolase variants having a novel amino acid sequence and, in general, at least one property which is substantially different from the same property of the enzyme encoded by the precursor carbonyl hydrolase DNA sequence. Such properties include proteolytic activity, substrate specificity, stability, altered pH profile and/or enhanced performance characteristics.

The present invention encompasses the substitution of any of the nineteen naturally occurring L-amino acids at the designated amino acid residue positions. Such substitutions can be made in any precursor subtilisin (procaryotic, eucaryotic, mammalian, etc.). Preferably, the substitution to be made at each of the identified amino acid residue positions include but are not limited to: substitutions at position 76 including D, H, E, G, F, K, P and N; substitutions at position 99 including D, T, N, Q, G and S; substitutions at position 101 including G, D, K, L, A, E, S and R; substitutions at position 103 including Q, T, D, E, Y, K, G, R, S and A; substitutions at position 104 including all nineteen naturally-occurring amino acids; substitutions at position 107 including V, L, M, Y, G, E, F, T, S, A, N and I; substitutions at position 123 including N, T, I, G, A, C and S; substitutions at position 27 including K, N, C, V and T; substitutions at position 105 including A, D, G, R and N; substitutions at position 107 including A, L, V, Y, G, F, T, S and A; substitutions at position 109 including S, K, R, A, N and D; substitutions at position 126 including A, F, I, V and G; substitutions at position 128 including G, L and A; substitutions at position 135 including A, F, I, S and V; substitutions at position 156 including D, E, A, G, Q and K; substitutions at position 166 including all nineteen naturally-occurring amino acids; substitutions at position 195 including E; substitutions at position 197 including E; substitutions at position 204 including A, G, C, S and D; substitutions at position 206 including L, Y, N, D and E; substitutions at position 210 including L, I, S, C and F; substitutions at position 216 including V, E, T and K; substitutions at position 217 including all nineteen naturally-occurring amino acids; substitutions at position 218 including S, A, G, T and V; substitutions at position 222 including all nineteen naturally-occurring amino acids; substitutions at position 260 including P, N, G, A, S, C, K and D; substitutions at position 265 including N, G, A, S, C, K, Y and H; and substitutions at position 274 including A and S. The specifically preferred amino acid(s) to be substituted at each such position are designated below in Table I. Although specific amino acids are shown in Table I, it should be understood that any amino acid may be substituted at the identified residues.

TABLE I

| Amino Acid Residue | Preferred Amino Acid to be Substituted/Inserted |
|---|---|
| +76 | D, H |
| +99 | D, T, N, G |
| +101 | R, G, D, K, L, A, E |
| +103 | A, Q, T, D, E, Y, K, G, R |
| +104 | I, Y, S, L, A, T, G, F, M, W, D, V, N |
| +107 | V, L, Y, G, F, T, S, A, N |
| +123 | S, T, I |
| +27 | K |
| +105 | A, D, |
| +109 | S, K, R |
| +126 | A, I, V, F |
| +128 | G, L |
| +135 | I, A, S |
| +156 | E, D, Q |
| +166 | D, G, E, K, N, A, F, I, V, L |
| +195 | E |
| +197 | E |
| +204 | A, G, C |
| +206 | L |
| +210 | I, S, C |
| +216 | V |
| +217 | H, I, Y, C, A, G, F, S, N, E, K |
| +218 | S |
| +222 | A, Q, S, C, I, K |
| +260 | P, A, S, N, G |
| +265 | N, A, G, S |
| +274 | A, S |

Further, the invention includes expression vectors containing such variant carbonyl hydrolase DNA sequences, as well as host cells transformed with such vectors which are capable of producing such variants. The invention also relates to detergent compositions comprising the carbonyl hydrolase variants of the invention.

BRIEF DESCRIPTION OF THE DRAWINGS

FIGS. 1A, 1B-1, 1B-2, and 1B-3 depict the DNA and amino acid sequence for *Bacillus amyloliquefaciens* subtilisin and a partial restriction map of this gene (Seq. ID No. 6).

FIG. 2 depicts the conserved amino acid residues among subtilisins from *Bacillus amyloliquefaciens* (BPN)' and *Bacillus lentus* (wild-type).

FIGS. 3A and 3B depict the amino acid sequence of four subtilisins. The top line represents the amino acid sequence of subtilisin from *Bacillus amyloliquefaciens* subtilisin (also sometimes referred to as subtilisin BPN') (Seq. ID No.7). The second line depicts the amino acid sequence of subtilisin from *Bacillus subtilis* (Seq. ID No.8). The third line depicts the amino acid sequence of subtilisin from *B. licheniformis* (Seq. ID No.9). The fourth line depicts the amino acid sequence of subtilisin from *Bacillus lentus* (also referred to as subtilisin 309 in PCT WO89/06279 (Seq. ID No.10). The symbol * denotes the absence of specific amino acid residues as compared to subtilisin BPN'.

FIG. 4 depicts the construction of plasmid GGA274.

FIG. 5 depicts the construction of GGT274 which is an intermediate to certain expression plasmids used in this application.

FIGS. 6A and 6B depict the DNA and amino acid sequence of subtilisin from *Bacillus lentus* (Seq. ID No.11). The mature subtilisin protein is coded by the codons beginning at the codon GCG (334–336) corresponding to Ala.

FIGS. 7A and 7B depict the DNA and amino acid sequence of a preferred embodiment of the invention (N76D/S103A/V104I) (Seq. ID No.12). The DNA in this figure has been modified by the methods described to encode aspartate at position 76, alanine at position 103 and isoleucine at position 104. The mature subtilisin variant protein is coded by the codons beginning at the codon GCG (334–336) corresponding to Ala.

FIG. 8 depicts the construction of vector pBCDAICAT.

FIG. 9 depicts the construction of vector pUCCATFNA.

FIG. 10 shows the stability of a preferred mutant enzyme compared to wild-type, in a liquid detergent formulation.

DETAILED DESCRIPTION OF THE INVENTION

It has been discovered that in vitro mutations in *B. lentus* subtilisin at an amino acid residue equivalent to +76 in *Bacillus amyloliquefaciens* subtilisin produces subtilisin variants exhibiting altered stability (e.g., modified autoproteolytic stability) over precursor subtilisins. (See Tables IV and VI.)

It has also been discovered that in vitro mutation at residues equivalent to +99, +101, +103, +104, +107, +123, +27, +105, +109, +126, +128, +135, +156, +166, +195, +197, +204, +206, +210, +216, +217, +218, +222, +260, +265 and/or +274 in *Bacillus amyloliquefaciens* subtilisin, alone or in combination with each other and in any combination with +76 mutations, produce subtilisin variants exhibiting altered proteolytic activity, altered thermal stability, altered pH profile, altered substrate specificity and/or altered performance characteristics.

Carbonyl hydrolases are enzymes which hydrolyze compounds containing 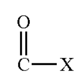 bonds in which X is oxygen or nitrogen. They include naturally-occurring carbonyl hydrolases and recombinant carbonyl hydrolases. Naturally-occurring carbonyl hydrolases principally include hydrolases, e.g., peptide hydrolases such as subtilisins or metalloproteases. Peptide hydrolases include α-aminoacylpeptide hydrolase, peptidylamino acid hydrolase, acylamino hydrolase, serine carboxypeptidase, metallocarboxypeptidase, thiol proteinase, carboxylproteinase and metalloproteinase. Serine, metallo, thiol and acid proteases are included, as well as endo and exo-proteases.

"Recombinant carbonyl hydrolase" refers to a carbonyl hydrolase in which the DNA sequence encoding the naturally-occurring carbonyl hydrolase is modified to produce a mutant DNA sequence which encodes the substitution, insertion or deletion of one or more amino acids in the carbonyl hydrolase amino acid sequence. Suitable modification methods are disclosed herein, and in U.S. Pat. No. 4,760,025 (RE 34,606), U.S. Pat. No. 5,204,015 and U.S. Pat. No. 5,185,258, the disclosure of which are incorporated herein by reference.

Subtilisins are bacterial or fungal carbonyl hydrolases which generally act to cleave peptide bonds of proteins or peptides. As used herein, "subtilisin" means a naturally-occurring subtilisin or a recombinant subtilisin. A series of naturally-occurring subtilisins is known to be produced and often secreted by various microbial species. Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from the amino to carboxy terminus, is aspartate-histidine-serine. In the chymotrypsin related proteases the relative order, however, is histidine-aspartate-serine. Thus, subtilisin herein refers to a serine protease having the catalytic triad of subtilisin related proteases. Examples include but are not limited to the subtilisins identified in FIG. 3 herein.

"Recombinant subtilisin" refers to a subtilisin in which the DNA sequence encoding the subtilisin is modified to produce a variant (or mutant) DNA sequence which encodes the substitution, deletion or insertion of one or more amino acids in the naturally-occurring subtilisin amino acid sequence. Suitable methods to produce such modification, and which may be combined with those disclosed herein, include those disclosed in U.S. Pat. No. 4,760,025 (RE 34,606), U.S. Pat. No. 5,204,015 and U.S. Pat. No. 5,185,258.

"Non-human carbonyl hydrolases" and the DNA encoding them may be obtained from many procaryotic and eucaryotic organisms. Suitable examples of procaryotic organisms include gram negative organisms such as E. coli or Pseudomonas and gram positive bacteria such as Micrococcus or Bacillus. Examples of eucaryotic organisms from which carbonyl hydrolase and their genes may be obtained include yeast such as Saccharomyces cerevisiae, fungi such as Aspergillus sp. and non-human mammalian sources such as, for example, bovine sp. from which the gene encoding the carbonyl hydrolase chymosin can be obtained. As with subtilisins, a series of carbonyl hydrolases can be obtained from various related species which have amino acid sequences which are not entirely homologous between the members of that series but which nevertheless exhibit the same or similar type of biological activity. Thus, non-human carbonyl hydrolase as used herein has a functional definition which refers to carbonyl hydrolases which are associated, directly or indirectly, with procaryotic and eucaryotic sources.

A "carbonyl hydrolase variant" has an amino acid sequence which is derived from the amino acid sequence of a "precursor carbonyl hydrolase." The precursor carbonyl hydrolases (such as a subtilisin) include naturally-occurring carbonyl hydrolases (subtilisin) and recombinant carbonyl hydrolases (subtilisin). The amino acid sequence of the carbonyl hydrolase variant is "derived" from the precursor hydrolase amino acid sequence by the substitution, deletion or insertion of one or more amino acids of the precursor amino acid sequence. Such modification is of the "precursor DNA sequence" which encodes the amino acid sequence of the precursor carbonyl hydrolase (subtilisin) rather than manipulation of the precursor carbonyl hydrolase (subtilisin) enzyme per se. Suitable methods for such manipulation of the precursor DNA sequence include methods disclosed herein, as well as methods known to those skilled in the art (see, for example, EP 0 328299, WO89/06279 and the US patents and applications already referenced herein).

Specific residues corresponding to position +76 in combination with one or more of the following positions +99, +101, +103, +104, +107, +123, +27, +105, +109, +126, +128, +135, +156, +166, +195, +197, +204, +206, +210, +216, +217, +218, +222, +260, +265 and/or +274 of Bacillus amyloliquefaciens subtilisin are identified herein for mutation. Preferably the modified residues are selected from the following combinations: 76/99; 76/101; 76/103; 76/104; 76/107; 76/123; 76/99/101; 76/99/103; 76/99/104; 76/101/103; 76/101/104; 76/103/104; 76/104/107; 76/104/123; 76/107/123; 76/99/101/103; 76/99/101/104; 76/99/103/104; 76/101/103/104; 76/103/104/123; 76/104/107/123; 76/99/101/103/104; 76/99/103/104/123; 76/99/101/103/104/123; 76/103/104/128; 76/103/104/260; 76/103/104/265; 76/103/104/197; 76/103/104/105; 76/103/104/135; 76/103/104/126; 76/103/104/107; 76/103/104/210; 76/103/104/126/265 and/or 76/103/104/222; and most preferably are 76/99; 76/104; 76/99/104; 76/103/104; 76/104/107; 76/101/103/104; 76/99/101/103/104 and 76/101/104. These amino acid position numbers refer to those assigned to the mature Bacillus amyloliquefaciens subtilisin sequence presented in FIG. 1. The invention, however, is not limited to the mutation of this particular subtilisin but extends to precursor carbonyl hydrolases containing amino acid residues at positions which are "equivalent" to the particular identified residues in Bacillus amyloliquefaciens subtilisin. In a preferred embodiment of the present invention, the precursor subtilisin is Bacillus lentus subtilisin and the substitutions, deletions or insertions are made at the equivalent amino acid residue in B. lentus corresponding to those listed above.

A residue (amino acid) of a precursor carbonyl hydrolase is equivalent to a residue of Bacillus amyloliquefaciens subtilisin if it is either homologous (i.e., corresponding in position in either primary or tertiary structure) or analogous to a specific residue or portion of that residue in Bacillus amyloliquefaciens subtilisin (i.e., having the same or similar functional capacity to combine, react, or interact chemically).

In order to establish homology to primary structure, the amino acid sequence of a precursor carbonyl hydrolase is directly compared to the Bacillus amyloliquefaciens subtilisin primary sequence and particularly to a set of residues known to be invariant in subtilisins for which sequence is known. FIG. 2 herein shows the conserved residues as between B. amyloliquefaciens subtilisin and B. lentus subtilisin. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of Bacillus amyloliquefaciens subtilisin are defined. Alignment of conserved residues preferably should conserve 100% of such residues. However, alignment of greater than 75% or as little as 50% of conserved residues is also adequate to define equivalent residues. Conservation of the catalytic triad, Asp32/His64/Ser221 should be maintained.

For example, in FIG. 3 the amino acid sequence of subtilisin from Bacillus amyloliquefaciens, Bacillus subtilis, Bacillus licheniformis (carlsbergensis) and Bacillus lentus are aligned to provide the maximum amount of homology between amino acid sequences. A comparison of these sequences shows that there are a number of conserved residues contained in each sequence. These conserved residues (as between BPN' and B. lentus) are identified in FIG. 2.

These conserved residues, thus, may be used to define the corresponding equivalent amino acid residues of Bacillus amyloliquefaciens subtilisin in other carbonyl hydrolases such as subtilisin from Bacillus lentus (PCT Publication No. WO89/06279 published Jul. 13, 1989), the preferred subtilisin precursor enzyme herein, or the subtilisin referred to as PB92 (EP 0 328 299), which is highly homologous to the preferred *Bacillus lentus* subtilisin. The amino acid sequences of certain of these subtilisins are aligned in FIGS. 3A and 3B with the sequence of *Bacillus amyloliquefaciens* subtilisin to produce the maximum homology of conserved residues. As can be seen, there are a number of deletions in the sequence of *Bacillus lentus* as compared to *Bacillus amyloliquefaciens* subtilisin. Thus, for example, the equivalent amino acid for Val165 in *Bacillus amyloliquefaciens* subtilisin in the other subtilisins is isoleucine for *B. lentus* and *B. licheniformis*.

Thus, for example, the amino acid at position +76 is asparagine (N) in both *B. amyloliquefaciens* and *B. lentus subtilisins*. In the preferred subtilisin variant of the invention, however, the amino acid equivalent to +76 in *Bacillus amyloliquefaciens* subtilisin is substituted with aspartate (D). A comparison of certain of the amino acid residues identified herein for substitution versus the most preferred substitution for each such position is provided in Table II for illustrative purposes.

TABLE II

|  | +76 | +99 | +101 | +103 | +104 | +107 | +123 |
|---|---|---|---|---|---|---|---|
| *B. amyloliquefaciens* (wild-type) | N | D | S | Q | Y | I | N |
| *B. lentus* (wild-type) | N | S | S | S | V | I | N |
| Most Preferred Substitution | D | D | R | A | I/Y | V | S |

Equivalent residues may also be defined by determining homology at the level of tertiary structure for a precursor carbonyl hydrolase whose tertiary structure has been determined by x-ray crystallography. Equivalent residues are defined as those for which the atomic coordinates of two or more of the main chain atoms of a particular amino acid residue of the precursor carbonyl hydrolase and *Bacillus amyloliquefaciens* subtilisin (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the carbonyl hydrolase in question to the *Bacillus amyloliquefaciens* subtilisin. The best model is the crystallographic model giving the lowest R factor for experimental diffraction data at the highest resolution available.

$$R \text{ factor} = \frac{\sum_h |Fo(h)| - |Fc(h)|}{\sum_h |Fo(h)|}$$

Equivalent residues which are functionally analogous to a specific residue of *Bacillus amyloliquefaciens* subtilisin are defined as those amino acids of the precursor carbonyl hydrolases which may adopt a conformation such that they either alter, modify or contribute to protein structure, substrate binding or catalysis in a manner defined and attributed to a specific residue of the *Bacillus amyloliquefaciens* subtilisin. Further, they are those residues of the precursor carbonyl hydrolase (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *Bacillus amyloliquefaciens* subtilisin. The coordinates of the three dimensional structure of *Bacillus amyloliquefaciens* subtilisin are set forth in EPO Publication No. 0 251 446 (equivalent to U.S. patent application Ser. No. 08/212,291, the disclosure of which is incorporated herein by reference) and can be used as outlined above to determine equivalent residues on the level of tertiary structure.

Some of the residues identified for substitution, insertion or deletion are conserved residues whereas others are not. In the case of residues which are not conserved, the replacement of one or more amino acids is limited to substitutions which produce a variant which has an amino acid sequence that does not correspond to one found in nature. In the case of conserved residues, such replacements should not result in a naturally-occurring sequence. The carbonyl hydrolase variants of the present invention include the mature forms of carbonyl hydrolase variants, as well as the pro- and preproforms of such hydrolase variants. The prepro-forms are the preferred construction since this facilitates the expression, secretion and maturation of the carbonyl hydrolase variants.

"Prosequence" refers to a sequence of amino acids bound to the N-terminal portion of the mature form of a carbonyl hydrolase which when removed results in the appearance of the "mature" form of the carbonyl hydrolase. Many proteolytic enzymes are found in nature as translational proenzyme products and, in the absence of post-translational processing, are expressed in this fashion. A preferred prosequence for producing carbonyl hydrolase variants, specifically subtilisin variants, is the putative prosequence of *Bacillus amyloliquefaciens* subtilisin, although other subtilisin prosequences may be used. In Examples 1 and 2 the putative prosequence from the subtilisin from *Bacillus lentus* (ATCC 21536) was used.

A "signal sequence" or "presequence" refers to any sequence of amino acids bound to the N-terminal portion of a carbonyl hydrolase or to the N-terminal portion of a prohydrolase which may participate in the secretion of the mature or pro forms of the hydrolase. This definition of signal sequence is a functional one, meant to include all those amino acid sequences encoded by the N-terminal portion of the subtilisin gene or other secretable carbonyl hydrolases which participate in the effectuation of the secretion of subtilisin or other carbonyl hydrolases under native conditions. The present invention utilizes such sequences to effect the secretion of the carbonyl hydrolase variants as defined herein. A preferred signal sequence used in the Examples comprises the first seven amino acid residues of the signal sequence from *Bacillus subtilis* subtilisin fused to the remainder of the signal sequence of the subtilisin from *Bacillus lentus* (ATCC 21536).

A "prepro" form of a carbonyl hydrolase variant consists of the mature form of the hydrolase having a prosequence operably linked to the amino terminus of the hydrolase and a "pre" or "signal" sequence operably linked to the amino terminus of the prosequence.

"Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

The "host cells" used in the present invention generally are procaryotic or eucaryotic hosts which preferably have been manipulated by the methods disclosed in U.S. Pat. No. 4,760,025 (RE 34,606) to render them incapable of secreting enzymatically active endoprotease. A preferred host cell for expressing subtilisin is the Bacillus strain BG2036 which is deficient in enzymatically active neutral protease and alkaline protease (subtilisin). The construction of strain BG2036 is described in detail in U.S. Pat. No. 5,264,366. Other host cells for expressing subtilisin include *Bacillus subtilis* I168 (also described in U.S. Pat. No. 4,760,025 (RE 34,606) and U.S. Pat. No. 5,264,366, the disclosure of which are incorporated herein by reference), as well as any suitable Bacillus strain such as *B. licheniformis, B. lentus*, etc.

Host cells are transformed or transfected with vectors constructed using recombinant DNA techniques. Such transformed host cells are capable of either replicating vectors encoding the carbonyl hydrolase variants or expressing the desired carbonyl hydrolase variant. In the case of vectors which encode the pre- or prepro-form of the carbonyl hydrolase variant, such variants, when expressed, are typically secreted from the host cell into the host cell medium.

"Operably linked," when describing the relationship between two DNA regions, simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the naturally-occurring precursor carbonyl hydrolase may be obtained in accord with the general methods known to those skilled in the art. The methods generally comprise synthesizing labeled probes having putative sequences encoding regions of the hydrolase of interest, preparing genomic libraries from organisms expressing the hydrolase, and screening the libraries for the gene of interest by hybridization to the probes. Positively hybridizing clones are then mapped and sequenced. The *B. lentus* gene used in the Examples was cloned as described in Example 1 of U.S. Pat. No. 5,185,258, the disclosure of which is incorporated herein. The BPN' gene used in Example 5 was cloned as described in Example 1 in RE 34,606, the disclosure of which is incorporated herein.

The cloned carbonyl hydrolase is then used to transform a host cell in order to express the hydrolase. The hydrolase gene is then ligated into a high copy number plasmid. This plasmid replicates in hosts in the sense that it contains the well-known elements necessary for plasmid replication: a promoter operably linked to the gene in question (which may be supplied as the gene's own homologous promoter if it is recognized, i.e., transcribed, by the host), a transcription termination and polyadenylation region (necessary for stability of the mRNA transcribed by the host from the hydrolase gene in certain eucaryotic host cells) which is exogenous or is supplied by the endogenous terminator region of the hydrolase gene and, desirably, a selection gene such as an antibiotic resistance gene that enables continuous cultural maintenance of plasmid-infected host cells by growth in antibiotic-containing media. High copy number plasmids also contain an origin of replication for the host, thereby enabling large numbers of plasmids to be generated in the cytoplasm without chromosomal limitations. However, it is within the scope herein to integrate multiple copies of the hydrolase gene into host genome. This is facilitated by procaryotic and eucaryotic organisms which are particularly susceptible to homologous recombination.

The genes used in the present examples are a natural *B. lentus* gene and a natural *B. amyloliquefaciens* gene. Alternatively, a synthetic gene encoding a naturally-occurring or mutant precursor carbonyl hydrolase (subtilisin) may be produced. In such an approach, the DNA and/or amino acid sequence of the precursor hydrolase (subtilisin) is determined. Multiple, overlapping synthetic single-stranded DNA fragments are thereafter synthesized, which upon hybridization and ligation produce a synthetic DNA encoding the precursor hydrolase. An example of synthetic gene construction is set forth in Example 3 of U.S. Pat. No. 5,204,015, the disclosure of which is incorporated herein by reference.

Once the naturally-occurring or synthetic precursor carbonyl hydrolase gene has been cloned, a number of modifications are undertaken to enhance the use of the gene beyond synthesis of the naturally-occurring precursor carbonyl hydrolase. Such modifications include the production of recombinant carbonyl hydrolases as disclosed in U.S. Pat. No. 4,760,025 (RE 34,606) and EPO Publication No. 0 251 446 and the production of carbonyl hydrolase variants described herein.

The following cassette mutagenesis method may be used to facilitate the construction and identification of the carbonyl hydrolase variants of the present invention, although other methods including site-directed mutagenesis may be used. First, the naturally-occurring gene encoding the hydrolase is obtained and sequenced in whole or in part. Then the sequence is scanned for a point at which it is desired to make a mutation (deletion, insertion or substitution) of one or more amino acids in the encoded enzyme. The sequences flanking this point are evaluated for the presence of restriction sites for replacing a short segment of the gene with an oligonucleotide pool which when expressed will encode various mutants. Such restriction sites are preferably unique sites within the hydrolase gene so as to facilitate the replacement of the gene segment. However, any convenient restriction site which is not overly redundant in the hydrolase gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction. Mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site.

Once the naturally-occurring DNA or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites.

As used herein, proteolytic activity is defined as the rate of hydrolysis of peptide bonds per milligram of active enzyme. Many well known procedures exist for measuring proteolytic activity (K. M. Kalisz, "Microbial Proteinases," *Advances in Biochemical Engineering/Biotechnology*, A. Fiechter ed., 1988). In addition to or as an alternative to modified proteolytic activity, the variant enzymes of the present invention may have other modified properties such as $K_m$, $k_{cat}$, $k_{cat}/K_m$ ratio and/or modified substrate specificity and/or modified pH activity profile. These enzymes can be tailored for the particular substrate which is anticipated to be present, for example, in the preparation of peptides or for hydrolytic processes such as laundry uses.

In one aspect of the invention the objective is to secure a variant carbonyl hydrolase having altered proteolytic activity as compared to the precursor carbonyl hydrolase, since increasing such activity (numerically larger) enables the use of the enzyme to more efficiently act on a target substrate. Also of interest are variant enzymes having altered thermal stability and/or altered substrate specificity as compared to the precursor. Preferably the carbonyl hydrolase to be mutated is a subtilisin. Specific amino acids useful to obtain such results in subtilisin-type carbonyl hydrolases at residues equivalent to +76, +99, +101, +103, +104, +107, +123 +27, +105, +109, +126, +128, +135, +156, +166, +195, +197, +204, +206, +210, +216, +217, +218, +222, +260, +265 and/or +274 or any combination thereof in *Bacillus amyloliquefaciens* subtilisin are presented in the Examples. In some instances, lower proteolytic activity may be desirable, for example a decrease in proteolytic activity would be useful where the synthetic activity of the carbonyl hydrolases is desired (as for synthesizing peptides). One may wish to decrease this proteolytic activity, which is capable of destroying the product of such synthesis. Conversely, in some instances it may be desirable to increase the proteolytic activity of the variant enzyme versus its precursor. Additionally, increases or decreases (alteration) of the stability of the variant, whether alkaline or thermal stability, may be,desirable. Increases or decreases in $k_{cat}$, $K_m$ or $k_{cat}/K_m$ are specific to the substrate used to determine these kinetic parameters.

In another aspect of the invention, it has been determined that residues equivalent to +76 in combination with a number of other modifications in subtilisin are important in modulating overall stability and/or proteolytic activity of the enzyme. Thus, as set forth in the Examples, the Asparagine (N) in *Bacillus lentus* subtilisin at equivalent position +76 can be substituted with Aspartate (D) in the preferred embodiment in combination with modification of one or more of the following amino acid residues +99, +101, +103, +104, +107, +123, +27, +105, +109, +126, +128, +135, +156, +166, +195, +197, +204, +206, +210, +216, +217, +218, +222, +260, +265 and/or +274, to produce enhanced stability and/or enhanced activity of the resulting mutant enzyme.

The most preferred embodiments of the invention are set forth in the Examples. These include the following specific combinations of substituted residues: N76D/S99D; N76D/V104I; N76D/S99D/V104I; N76D/S103A/V104I; N76D/V104I/I107V; N76D/V104Y/I107V and N76D/S101R/S103A/V104I. Also described in the Examples are all mutant combinations claimed in the present invention. These substitutions are preferably made in *Bacillus lentus* (recombinant or native-type) subtilisin, although the substitutions may be made in any *Bacillus subtilisin*.

Based on the results obtained with this and other variant subtilisins, it is apparent that residues in carbonyl hydrolases (preferably subtilisin) equivalent to positions +76, +99, +101, +103, +104, +107, +123, +27, +105, +109, +126, +28, +135, +156, +166, +195, +197, +204, +206, +210, +216, +217, +218, +222, +260, +265 and/or +274 in *Bacillus amyloliquefaciens* are important to the proteolytic activity, performance and/or stability of these enzymes and the cleaning or wash performance of such variant enzymes.

Many of the carbonyl hydrolase variants of the invention, especially subtilisin, are useful in formulating various detergent compositions. A number of known compounds are suitable surfactants useful in compositions comprising the carbonyl hydrolase mutants of the invention. These include nonionic, anionic, cationic, anionic or zwitterionic detergents, as disclosed in U.S. Pat. No. 4,404,128 to Barry J. Anderson and U.S. Pat. No. 4,261,868 to Jiri Flora, et al. A suitable detergent formulation is that described in Example 7 of U.S. Pat. No. 5,204,015 (previously incorporated by reference). The art is familiar with the different formulations which can be used as cleaning compositions. In addition to typical cleaning compositions, it is readily understood that the subtilisin variants of the present invention may be used for any purpose that native or wild-type subtilisins are used. Thus, these variants can be used, for example, in bar or liquid soap applications, dishcare formulations, contact lens cleaning solutions or products, peptide hydrolysis, waste treatment, textile applications, as fusion-cleavage enzymes in protein production, etc. The variants of the present invention may comprise enhanced performance in a detergent composition (as compared to the precursor). As used herein, enhanced performance in a detergent is defined as increasing cleaning of certain enzyme sensitive stains such as grass or blood, as determined by usual evaluation after a standard wash cycle.

Subtilisins of the invention can be formulated into known powdered and liquid detergents having pH between 6.5 and 12.0 at levels of about 0.01 to about 5% (preferably 0.1% to 0.5%) by weight. These detergent cleaning compositions can also include other enzymes such as known proteases, amylases, cellulases, lipases or endoglycosidases, as well as builders and stabilizers.

The addition of subtilisins of the invention to conventional cleaning compositions does not create any special use limitation. In other words, any temperature and pH suitable for the detergent is also suitable for the present compositions as long as the pH is within the above range, and the temperature is below the described subtilisin's denaturing temperature. In addition, subtilisins of the invention can be used in a cleaning composition without detergents, again either alone or in combination with builders and stabilizers.

The following is presented by way of example and is not to be construed as a limitation to the scope of the claims.

EXAMPLE 1

Construction for the Expression of GG36 Gene in *B. subtilis*

The cloning and the construction for expression of the subtilisin gene from *B. lentus* was performed essentially the same as that described in U.S. Pat. No. 5,185,258. The plasmid GGA274 (described in FIG. 4 herein) was further modified in the following manner, as shown in FIG. 5. The PstI site that was introduced during the construction of the GGA274 plasmid was removed by the oligonucleotide directed mutagenesis described below, with an oligonucleotide having the following sequence: 5' GAAGCTGCA ACTCGTTAAA 3' (Seq. ID No.1). The underlined "A" residue eliminated the recognition sequence of restriction enzyme PstI and changed the corresponding amino acid residue from alanine to threonine at position 274. Threonine at position 274 is the wild-type residue originally found in the cloned *B. lentus* subtilisin gene sequences. The DNA segment encoding subtilisin was excised from the plasmid GGA274 or its derivatives (GGT274 shown in FIG. 5) by EcoRI and BamHI digest. The DNA fragment was subcloned back into Bacteriophage M13-based vectors, such as MP19, for mutagenesis. After mutagenesis, the EcoRI and HindIII digest, followed by cloning, were performed to move the mutated subtilisin gene back into an expression plasmid like GGA274 for the expression and the recovery of mutated subtilisin proteins.

EXAMPLE 2

Oligonucleotide-Directed Mutagenesis

Oligonucleotide-directed mutagenesis was performed as described in Zoller, M., et al. (1983), *Methods Enzymol.*, 100:468–500. As an example, a synthetic oligonucleotide of the sequence 5' GCTGCTCTAGACAATTCG 3' (Seq. ID No.2) was used to change the amino acid residue at position 76 from asparagine (N) to aspartic acid (D), or N76D. The underlined "G" and "C" residues denote changes from the wild-type gene sequence. The CA keeps the leucine at position +75 and changes the amino acid sequence to introduce an XbaI recognition site of the XbaI restriction enzyme (TCTAGA), while the change at GAC changes asparagine at +76 to aspartate.

For mutagenesis at positions 99, 101, 103 and 104, different oligonucleotides can be used depending on the combination of mutations desired. For example, an oligonucleotide of the sequence 5' GTATTAGGGGCGGACGGT CGAGGCGCCATCAGCTCGATT 3' (Seq. ID No.3) was used to simultaneously make the following changes: S99D; S101R; S103A and V104I in a single subtilisin molecule. Similarly, oligonucleotides of the sequence 5' TCAGGT-TCGGTCTCGAGCGTTGCCCAAGGATTG 3' (Seq. ID No.4) and 5' CACGTTGCTAGCTTGAGTTTAG 3' (Seq. ID No.5) were utilized to generate I107V and N123S, respectively. Again, the underlined residues denote changes from wild-type sequences which produced desired changes either in amino acid sequences or restriction enzyme recognition sequences.

EXAMPLE 3

Proteolytic Activity of Subtilisin Variants

Following the methods of Example 2, the variants listed in Table III were made. Proteolytic activity of each of these subtilisin variants is shown in Table III. The kinetic parameters $k_{cat}$, $K_M$, and $k_{cat}/K_M$ were measured for hydrolysis of the synthetic peptide substrate succinyl-L-Ala-L-Ala-L-Pro-L-Phe-p-nitroanilide using the method described in P. Bonneau, et al. (1991) *J. Am. Chem. Soc.*, Vol. 113, No. 3, p. 1030. Briefly, a small aliquot of subtilisin variant stock solution was added to a 1 cm cuvette containing substrate dissolved in 0.1M Tris-HCL buffer, pH 8.6, and thermostated at 25° C. The reaction progress was followed spectrophotometrically by monitoring the absorbance of the reaction product p-nitroaniline at 410 nm. Kinetic parameters were obtained by using a non-linear regression algorithm to fit the reaction velocity and product concentration for each reaction to the Michaelis-Menten equation.

TABLE III

Kinetic Parameters $k_{cat}$, $K_M$ and $k_{cat}/K_M$
Measured for *Bacillus lentus* Subtilisin and Variants

| Enzyme | $k_{cat}$ (s$^{-1}$) | $K_M$ (M) | $k_{cat}/K_M$ (s$^{-1}$M$^{-1}$) |
|---|---|---|---|
| *B. lentus* Subtilisin | 170 | 0.00078 | 2.18 × 10$^5$ |
| N76D | 219 | 0.0008 | 2.74 × 10$^5$ |
| N76D/S99D | 88 | 0.00061 | 1.44 × 10$^5$ |
| N76D/S103A | 400 | 0.0014 | 2.86 × 10$^5$ |
| N76D/V104I | 459 | 0.0011 | 4.17 × 10$^5$ |
| N76D/I107V | 219 | 0.0011 | 1.99 × 10$^5$ |
| N76D/N123S | 115 | 0.0018 | 6.40 × 10$^4$ |
| N76D/S99D/S101R | 146 | 0.00038 | 3.84 × 10$^5$ |
| N76D/S99D/S103A | 157 | 0.0012 | 1.31 × 10$^5$ |
| N76D/S99D/V104I | 247 | 0.00097 | 2.55 × 10$^5$ |
| N76D/S101R/S103A | 405 | 0.00069 | 5.90 × 10$^5$ |
| N76D/S101R/V104I | 540 | 0.00049 | 1.10 × 10$^6$ |
| N76D/S103A/V104I | 832 | 0.0016 | 5.20 × 10$^5$ |
| N76D/V104I/I107V | 497 | 0.00045 | 1.10 × 10$^6$ |
| N76D/V104Y/I107V | 330 | 0.00017 | 1.90 × 10$^6$ |
| N76D/V104I/N123S | 251 | 0.0026 | 9.65 × 10$^4$ |
| N76D/I107V/N123S | 147 | 0.0035 | 4.20 × 10$^4$ |
| N76D/S99D/S101R/S103A | 242 | 0.00074 | 3.27 × 10$^5$ |
| N76D/S99D/S101R/V104I | 403 | 0.00072 | 5.60 × 10$^5$ |
| N76D/S99D/S103A/V104I | 420 | 0.0016 | 2.62 × 10$^5$ |
| N76D/S101R/S103A/V104I | 731 | 0.00065 | 1.12 × 10$^6$ |
| N76D/S103A/V104I/N123S | 321 | 0.0026 | 1.23 × 10$^5$ |
| N76D/V104I/I107V/N123S | 231 | 0.003 | 7.70 × 10$^4$ |
| N76D/S99D/S101R/S103A/V104I | 624 | 0.00098 | 6.37 × 10$^5$ |
| N76D/S99D/S103A/V104I/N123S | 194 | 0.0043 | 4.51 × 10$^4$ |
| N76D/S99D/S101R/S103A/V104I/N123S | 311 | 0.0023 | 1.35 × 10$^5$ |

The results listed in Table III indicate that all of the subtilisin variants tested retain proteolytic activity. Further, detailed analysis of the data reveal that proteolytic activity was significantly altered for *Bacillus lentus* subtilisin by the various combinations of substitutions at amino acid residues equivalent to positions 76, 99, 101, 103, 104, 107 and 123 in *Bacillus amyloliquefaciens*.

EXAMPLE 4

Thermal Stability of Subtilisin Variants

A comparison of thermal stability observed for *Bacillus lentus* subtilisin and the variants of the present invention made by the process of Example 2 is shown in Table IV. Purified enzyme, 15 ug/ml in 0.1 M glycine 0.01% Tween-80 pH 10.0, with or without 50 mM CaCl$_2$, was aliquotted into small tubes and incubated at 10° C. for 5 minutes, 10° C. to 60° C. over 1 minute, and 60° C. for 20 minutes. Tubes were then placed on ice for 10 minutes. Aliquots from the tubes were assayed for enzyme activity by addition to 1 cm cuvettes containing 1.2 mM of the synthetic peptide substrate succinyl-L-ala-L-Ala-L-Pro-L-Phe-p-nitroanilide dissolved in 0.1 M tris-HCL buffer, pH 8.6, thermostatted at 25° C. The initial linear reaction velocity was followed spectrophotometrically by monitoring the absorbance of the reaction product p-nitroaniline at 410 nm as a function of time. Data are presented as percent activity prior to heating. The results listed in Table IV indicate that a vast majority of variants exhibit thermal stability comparable to *Bacillus lentus* subtilisin (24 out of 26) in the test condition with 50 mM CaCl$_2$ added. In the test condition without 50 mM CaCl$_2$ added, a vast majority of variants (19 out of 26) are significantly more stable than *Bacillus lentus* subtilisin. Further, the variants N76D/S99D, N76D/V104I, N76D/S99D/V104I, N76D/S103A/V104I, N76D/V104I/I107V, N76D/V104Y/I107V and N76D/S101R/S103A/V104I are significantly more stable than the single substitution variant N76D in the test condition without 50 mM CaCl$_2$ added.

TABLE IV

Thermal Stability Measured for *Bacillus lentus* Subtilisin and Variants At pH 10, 60° C., +/− 50 mM CaCl$_2$ Added

| Enzyme | % Initial Activity Remaining | |
|---|---|---|
| | −CaCl$_2$ | +CaCl$_2$ |
| *B. lentus* Subtilisin | 2 | 96 |
| N76D | 34 | 97 |
| N76D/S99D | 49 | 98 |
| N76D/S103A | 26 | 92 |
| N76D/V104I | 58 | 98 |
| N76D/I107V | 32 | 96 |
| N76D/N123S | 0 | 97 |
| N76D/S99D/S101R | 30 | 100 |
| N76D/S99D/S103A | 36 | 100 |
| N76D/S99D/V104I | 48 | 97 |
| N76D/S101R/S103A | 26 | 100 |
| N76D/S101R/V104I | 38 | 100 |
| N76D/S103A/V104I | 58 | 100 |
| N76D/V104I/I107V | 60 | 97 |
| N76D/V104Y/I107V | 48 | 74 |
| N76D/V104I/N123S | 0 | 98 |
| N76D/I107V/N123S | 16 | 100 |
| N76D/S99D/S101R/S103A | 38 | 100 |
| N76D/S99D/S101R/V104I | 33 | 100 |
| N76D/S99D/S103A/V104I | 38 | 98 |
| N76D/S101R/S103A/V104I | 40 | 99 |
| N76D/S103A/V104I/N123S | 1 | 98 |
| N76D/V104I/I107V/N123S | 3 | 99 |
| N76D/S99D/S101R/S103A/V104I | 36 | 99 |
| N76D/S99D/S103A/V104I/N123S | 2 | 95 |
| N76D/S99D/S101R/S103A/V104I/N123S | 0 | 100 |

EXAMPLE 5

Oligonucleotide-Directed Mutagenesis with Single-Stranded DNA Template Generated from Phagemid A. Construction of *B. lentus* Variants The mutagenesis protocol was essentially the same as described above in Example 2. The single-stranded DNA template was generated by phagemid method. To construct the phagemid vector for generating the single-stranded DNA template we first constructed the vector pBCDAICAT. The flow chart of vector construction is outlined in FIG. 8. First, the ClaI to ClaI fragment encoding the CAT gene from pC194 plasmid (Horinouchi, S. and Weisblum, B., *J. Bacteriol.*, 150:8–15, 1982) was cloned into the AccI site of polylinker region of pUC19 (New England BioLabs, Beverly, Mass.) to make plasmid PUCCHL and the EcoRI-DraI 0.6 KB fragment from the 5' end of the GG36DAI encoding DNA was cloned into the EcoRI and EcoRV sites of PBSKS plasmid (Stratagene, Inc., San Diego, Calif.) to make pBC2SK5. The single EcoRI site of the plasmid pBC2SK5 was eliminated by EcoRI digestion, followed by filling in catalyzed-by-T4 DNA polymerase, and religation to generate the plasmid pBC2SK-5R which does not have the EcoRI site. The EcoRI-DraI fragment which was cloned into pBCSK-5R was isolated as a PstI-HindIII fragment and cloned into the PstI-HindIII site of the PUCCHL (part of the polylinker of pUC19) to generate plasmid pUCCHL5R. The encoding sequence of GG36DAI gene was excised as an EcoRI-BamHI fragment and cloned into the EcoRI-BamHI sites of pUCCHL5R to make pUCCAT. The large EcoRI-HindIII fragment of pUCCAT was then cloned into the EcoRI and HindIII sites of BS2KS+ to generate the plasmid pBCDAICAT.

To generate single-stranded DNA, *E. coli*-containing PBCDAICAT were infected with phage R408 (obtained from Stratagene, San Diego, Calif.) following the protocol described in Russel, M., Kidd, S. and Kelley, M. R., GENE 45:333–338, 1986. Once the single-stranded DNA template was available, standard mutagenesis methods as described above in Example 2 were carried out. The construction of certain mutants is detailed below for illustrative purposes.

For the construction of *B. lentus* (GG36) N76D/S103A/V104I/L217H, an EcoRI-BamHI DNA fragment encoding GG36 N76D/S103A/V104I was used in the construction of pUCCAT (see FIG. 8) to generate the plasmid pBCDAICAT. After the single-stranded DNA template was made following the protocol described above, a mutagenesis primer with the following sequence

```
                             (Seq. ID No.13)
              *  ***  **  x ClaI
5' TAT GCC AGC CAC AAC GGT ACT TCG ATG GCT 3'
``` was used to make the L217H. As before, the underlined residues denote the nucleotide changes that were made and the x ClaI indicates that the existing ClaI site was eliminated after the mutagenesis. The mutagenesis protocol was as described in Example 2. After the mutagenesis, plasmid DNA was first screened for the elimination of the ClaI site and those clones missing the ClaI site were subjected to DNA sequence analysis to verify the DNA sequence which made the L to H change at the 217th amino acid residue.

B. Construction of BPN' Variants and their Expression in *B. subtilis*

The construction of *B. amyloliquefaciens* (BPN') N76D/Q103A/Y104I/Y217L was done in a similar fashion except in two consecutive steps. N76D was first introduced into BPN' Y217L to make BPN' N76D/Y217L and a second mutagenesis was done to convert BPN' N76D/Y217L to BPN' N76D/Q103A/Y104I/Y217L. To generate the single-stranded DNA template for the first mutagenesis, an EcoRI-BamHI fragment encoding BPN' Y217L subtilisin (derived from the Y217L plasmid described in Wells, J., et al., *PNAS*, 84, 5167, 1087) was used to construct a plasmid pUCCA-TFNA (see FIG. 9). The pUCCATFNA plasmid containing BPN' Y217L was used to construct the pBCFNACAT plasmid (FIG. 9). Single-stranded DNA was generated as described above. To generate BPN' N76D/Y217L, an oligonucleotide primer with the sequence

```
                             (Seq. ID No.14)
              *  ***  **  x XbaI
5' C ACA GTT GCG GCT CTA GAT AAC TCA ATC GGT G 3'
``` was used to generate the change N76D. Single-stranded DNA was then prepared from the pBCFNACAT plasmid containing the BPN' N76D/Y217L (the pBCFNACAT plasmid after N76D mutagenesis) and mutagenized with another oligonucleotide with the sequence

```
                                    (Seq. ID No.15)
                              *  ***  ** x PvuII
        5' GCT GAC GGT TCC GGC GCT ATT AGT TGG ATC ATT 3'
``` to obtain BPN' N76D/Q103A/Y104I/Y217L. All steps involved in the cloning, the single-stranded DNA preparation, the mutagenesis, and the screening for mutants were carried out as described above.

Expression of the BPN' gene and its variants were achieved by integrating plasmid DNA (pBCFNACAT containing the different variants' BPN' gene) directly into a protease-deficient strain of Bacillus subtilis as described in RE 34,606.

Numerous variants were made as per the teachings of Examples 2 and 5. Kinetics data and stability data were generated for such variants. The kinetics data mere generated using the methods described in Example 3 and are provided in Table V. The stability data were generated as detailed herein. Results are shown in Table VI.

Thermal Stability Assay Procedure

Purified enzyme was buffer-exchanged into 0.1 M glycine pH 10.0, 0.01% Tween-80 by applying the enzyme to a column consisting of Sephadex G-25 equilibrated with this buffer and eluting the enzyme from the column using the same buffer.

To a tube containing 0.1 M glycine, 0.01% Tween-80 pH 10.0 thermostatted at 60° C., the buffer-exchanged enzyme was added to give a final enzyme concentration of 15 ug/ml.

Aliquots were removed from the 60° C. incubation at various times and immediately assayed for enzyme activity by addition to a 1 cm cuvette containing 1.2 mM of the synthetic peptide substrate succinyl-L-Ala-L-Ala-L-Pro-L-Phe-p-nitroanilide dissolved in 0.1 M tris-HCL buffer, pH 8.6, thermostatted at 25° C. The initial linear reaction velocity was followed spectrophotometrically by monitoring the absorbance of the reaction product p-nitroaniline at 410 nm as a function of time.

Half-life, which is the length of time required for 50% enzyme inactivation, was determined from the first-order plot of reaction velocity as a function of the time of incubation at 60° C.

The data are presented in Table VI as percent of the half-life determined for Bacillus lentus subtilisin (GG36) under identical conditions.

TABLE V

| Enzyme | kcat ($s^{-1}$) | KM (mM) | kcat/KM ($s^{-1}M^{-1}$) |
|---|---|---|---|
| B. lentus subtilisin | 170 | 0.78 | 2.20E+05 |
| N76D/S103G/V104I* | 380 | 1.4 | 2.70E+05 |
| N76D/S103A/V104F | 730 | 0.33 | 2.20E+06 |
| N76D/S103A/V104N | 790 | 2.8 | 2.80E+05 |
| N76D/S103A/V104S | 170 | 0.83 | 2.00E+05 |
| N76D/S103A/V104T | 370 | 1.9 | 2.00E+05 |
| N76D/S103A/V104W | 880 | 0.31 | 2.80E+06 |
| N76D/S103A/V104Y | 690 | 0.5 | 1.40E+06 |
| K27R/N76D/V104Y/N123S | 500 | 1.2 | 4.20E+05 |
| N76D/S101G/S103A/V104I* | 620 | 1.3 | 4.80E+05 |
| N76D/S103A/V104I/S105A* | 550 | 1.3 | 4.20E+05 |
| N76D/S103A/V104I/S105D* | 440 | 1.7 | 2.60E+05 |
| N76D/S103A/V104T/I107A* | 120 | 5.7 | 2.10E+04 |
| N76D/S103A/V104T/I107L* | 310 | 3.2 | 9.70E+04 |
| N76D/S103A/V104I/L126A | 90 | 2.2 | 4.10E+04 |
| N76D/S103A/V104I/L126F | 180 | 1.9 | 9.50E+04 |

TABLE V-continued

| Enzyme | kcat ($s^{-1}$) | KM (mM) | kcat/KM ($s^{-1}M^{-1}$) |
|---|---|---|---|
| N76D/S103A/V104I/L126I | 100 | 2.4 | 4.20E+04 |
| N76D/S103A/V104I/L126V | 64 | 3.2 | 2.00E+04 |
| N76D/S103A/V104I/S128G* | 560 | 1.7 | 3.30E+05 |
| N76D/S103A/V104I/S128L* | 430 | 3.8 | 1.10E+05 |
| N76D/S103A/V104I/L135A | 140 | 0.76 | 1.80E+05 |
| N76D/S103A/V104I/L135F | 390 | 0.69 | 5.70E+05 |
| N76D/S103A/V104I/L135I | 110 | 0.73 | 1.50E+05 |
| N76D/S103A/V104I/L135V | 140 | 0.86 | 1.60E+05 |
| N76D/S103A/V104I/S156E* | 170 | 2.6 | 6.50E+04 |
| N76D/S103A/V104I/S166D* | 160 | 3.5 | 4.60E+04 |
| N76D/S103A/V104I/D197E | 510 | 1.4 | 3.60E+05 |
| N76D/S103A/V104I/N204A* | 530 | 1.1 | 4.80E+05 |
| N76D/S103A/V104I/N204G* | 580 | 1.4 | 4.10E+05 |
| N76D/S103A/V104I/N204C* | 370 | 1.3 | 2.90E+05 |
| N76/S103A/V104I/P210I* | 500 | 1.2 | 4.20E+05 |
| N76D/S103A/V104I/L217H* | 80 | 0.63 | 1.30E+05 |
| N76D/S103A/V104I/M222A | 70 | 3.1 | 2.30E+04 |
| N76D/S103A/V104I/M222S | 80 | 3.1 | 2.60E+04 |
| N76D/S103A/V104I/T260P | 660 | 1.5 | 4.40E+05 |
| N76D/S103A/V104I/S265N | 590 | 1.3 | 4.50E+05 |
| K27R/N76D/V104Y/I107V/N123S | 220 | 1.4 | 1.60E+05 |
| K27R/N76D/V104Y/N123S/D197E | 430 | 1.1 | 3.90E+05 |
| K27R/N76D/V104Y/N123S/N204C | 400 | 1.1 | 3.60E+05 |
| K27R/N76D/V104Y/N123S/Q206L | 440 | 1.2 | 3.70E+05 |
| K27R/N76D/V104Y/N123S/S216V | 440 | 1.2 | 3.70E+05 |
| K27R/N76D/V104Y/N123S/N218S | 760 | 0.98 | 7.80E+05 |
| K27R/N76D/V104Y/N123S/T260P | 410 | 1.2 | 3.40E+05 |
| K27R/N76D/V104Y/N123S/T274A | 390 | 1 | 3.90E+05 |
| N76D/S103A/V104I/L126F/S265N | 170 | 2.1 | 8.10E+04 |
| N76D/S103A/V104I/S156E/S166D* | 40 | 6.3 | 6.40E+03 |
| K27R/N76D/V104Y/N123S/G195E/G197E | 410 | 0.98 | 4.20E+05 |
| K27R/N76D/V104Y/N123S/G195E/N218S | 540 | 0.66 | 8.20E+05 |
| K27R/N76D/V104Y/N123S/D197E/N218S | 770 | 0.79 | 9.80E+05 |
| K27R/N76D/V104Y/N123S/N204C/N218S | 610 | 0.99 | 6.20E+05 |
| K27R/N76D/V104Y/N123S/Q206L/N218S | 580 | 0.78 | 7.40E+05 |
| K27R/N76D/V104Y/N123S/N218S/T260P | 660 | 1 | 6.60E+05 |
| K27R/N76D/V104Y/N123S/N218S/T274A | 590 | 0.89 | 6.60E+05 |
| K27R/N76D/V104Y/Q109S/N123S/N218S/T274A | 520 | 1 | 5.20E+05 |
| K27R/N76D/V104Y/N123S/G195E/D197E/N218S | 460 | 0.65 | 7.10E+05 |
| B. amyloliquefaciens subtilisin (BPN') | 50 | 0.14 | 3.60E+05 |
| BPN'-N76D/Y217L* | 380 | 0.46 | 8.30E+05 |

*These mutants made as per Example 5, all others made as per Example 2

TABLE VI

| Enzyme | Thermal Stability (% half-life of native enzyme) |
|---|---|
| B. lentus subtilisin | 100 |
| N76D | 590 |
| N76D/S99D | 840 |
| N76D/S103A | 390 |
| N76D/V104I | 660 |
| N76D/I107V | 710 |
| N76D/N123S | 70 |
| N76D/S99D/S101R | 610 |
| N76D/S99D/S103A | 590 |
| N76D/S99D/V104I | 910 |
| N76D/S101R/S103A | 930 |
| N76D/S101R/V104I | 500 |
| N76D/S103A/V104I | 460 |
| N76D/S103G/V104I* | 370 |
| N76D/S103A/V104F | 480 |
| N76D/S103A/V104N | 230 |
| N76D/S103A/V104S | 230 |
| N76D/S103A/V104T | 370 |
| N76D/S103A/V104W | 280 |
| N76D/S103A/V104Y | 400 |
| N76D/V104I/I107V | 940 |
| N76D/V104Y/I107V | 820 |

TABLE VI-continued

| Enzyme | Thermal Stability (% half-life of native enzyme) |
|---|---|
| N76D/V104I/N123S | 80 |
| N76D/I107V/N123S | 150 |
| K27R/N76D/V104Y/N123S | 100 |
| N76D/S99D/S101R/S103A | 570 |
| N76D/S99D/S101R/V104I | 1000 |
| N76D/S99D/S103A/V104I | 680 |
| N76D/S101G/S103A/V104I* | 390 |
| N76D/S101R/S103A/V104I | 470 |
| N76D/S103A/V104I/S105A* | 360 |
| N76D/S103A/V104I/S105D* | 370 |
| N76D/S103A/V104T/I107A* | 270 |
| N76D/S103A/V104T/I107L* | 230 |
| N76D/S103A/V104I/N123S | 110 |
| N76D/V104I/I107V/N123S | 220 |
| N76D/S103A/V104I/L126A | 270 |
| N76D/S103A/V104I/L126F | 950 |
| N76D/S103A/V104I/L126I | 410 |
| N76D/S103A/V104I/L126V | 320 |
| N76D/S103A/V104I/S128G* | 640 |
| N76D/S103A/V104I/S128L* | 760 |
| N76D/S103A/V104I/L135A | 230 |
| N76D/S103A/V104I/L135F | 200 |
| N76D/S103A/V104I/L135I | 510 |
| N76D/S103A/V104I/L135V | 500 |
| N76D/S103A/V104I/S156E* | 120 |
| N76D/S103A/V104I/S166D* | 590 |
| N76D/S103A/V104I/D197E | 460 |
| N76D/S103A/V104I/N204A* | 230 |
| N76D/S103A/V104I/N204G* | 240 |
| N76D/S103A/V104I/N204C* | 500 |
| N76D/S103A/V104I/P210I* | 1370 |
| N76D/S103A/V104I/L217H* | 60 |
| N76D/S103A/V104I/M222A | 520 |
| N76D/S103A/V104I/M222S | 490 |
| N76D/S103A/V104I/T260P | 490 |
| N76D/S103A/V104I/S265N | 360 |
| K27R/N76D/V104Y/I107V/N123S | 210 |
| K27R/N76D/V104Y/N123S/D197E | 120 |
| K27R/N76D/V104Y/N123S/N204C | 110 |
| K27R/N76D/V104Y/N123S/Q206L | 380 |
| K27R/N76D/V104Y/N123S/S216V | 140 |
| K27R/N76D/V104Y/N123S/N218S | 270 |
| K27R/N76D/V104Y/N123S/T260P | 40 |
| K27R/N76D/V104Y/N123S/T274A | 60 |
| N76D/S99D/S101R/S103A/V104I | 590 |
| N76D/S99D/S103A/V104I/N123S | 110 |
| N76D/S103A/V104I/L126F/S265N | 810 |
| N76D/S103A/V104I/S156E/S166D* | 220 |
| K27R/N76D/V104Y/N123S/G195E/G197E | 90 |
| K27R/N76D/V104Y/N123S/G195E/N218S | 250 |
| K27R/N76D/V104Y/N123S/D197E/N218S | 270 |
| K27R/N76D/V104Y/N123S/N204C/N218S | 460 |
| K27R/N76D/V104Y/N123S/Q206L/N218S | 1400 |
| K27R/N76D/V104Y/N123S/N218S/T260P | 310 |
| K27R/N76D/V104Y/N123S/N218S/T274A | 180 |
| N76D/S99D/S101R/S103A/V104I/N123S | 90 |
| K27R/N76D/V104Y/Q109S/N123S/N218S/T274A | 230 |
| K27R/N76D/V104Y/N123S/G195E/D197E/N218S | 240 |
| *B. amyloliquefaciens* subtilisin (BPN') | 100 |
| BPN'-N76D/Y217L* | 420 |

*These mutants made as per Example 5, all others made as per Example 2

EXAMPLE 6

Wash Performance Test

The wash performance of the variants described in the previous examples was evaluated by measuring the removal of stain from EMPA 116 (blood/milk/carbon black on cotton) cloth swatches (Testfabrics, Inc., Middlesex, N.J. 07030).

Six EMPA 116 swatches, cut to 3×4½ inches with pinked edges, were placed in each pot of a Model 7243S Terg-O-Tometer (United States Testing Co., Inc., Hoboken, N.J.) containing 1000 ml of water, 15 gpg hardness ($Ca^{++}:Mg^{++}::3:1::w:w$), 7 g of detergent, and enzyme as appropriate. The detergent base was WFK1 detergent from wfk-Testgewebe GmbH, Adlerstrasse 42, Postfach 13 07 62, D-47759 Krefeld, Germany:

| Component | % of Final Formulation |
|---|---|
| Zeolite A | 25% |
| Sodium sulfate | 25% |
| Soda Ash | 10% |
| Linear alkylbenzenesulfonate | 8.8% |
| Alcohol ethoxylate (7–8 EO) | 4.5% |
| Sodium soap | 3% |
| Sodium silicate ($SiO_2:Na_2O::3.3:1$) | 3% |

To this base detergent, the following additions were made:

| Component | % of Final Formulation |
|---|---|
| Sodium perborate monohydrate | 13% |
| Copolymer (Sokalan CP5) | 4% |
| TAED (Mykon ATC Green) | 3% |
| Enzyme | 0.5% |
| Brightener (Tinopal AMS-GX) | 0.2% |

Sodium perborate monohydrate was obtained from Degussa Corporation, Ridgefield-Park, N.J. 07660. Sokalan CP5 was obtained from BASF Corporation, Parsippany, N.J. 07054. Mykon ATC Green (TAED, tetraacetylethylenediamine) was obtained from Warwick International, Limited, Mostyn, Holywell, Clwyd CH8 9HE, England. Tinopal AMS GX was obtained from Ciba-Geigy Corporation, Greensboro, N.C. 27419.

Six EMPA 116 swatches were washed in detergent with enzyme for 30 minutes at 60° C. and were subsequently rinsed twice for 5 minutes each time in 1000 ml water. Enzymes were added at final concentrations of 0.05 to 1 ppm for standard curves, and 0.25 ppm for routine analyses. Swatches were dried and pressed, and the reflectance from the swatches was measured using the L value on the L*a*b* scale of a Minolta Chroma Meter, Model CR-200 (Minolta Corporation, Ramsey, N.J. 07446). Performance is reported as a percentage of the performance of *B. lentus* (GG36) protease and was calculated by dividing the amount of *B. lentus* (GG36) protease by the amount of variant protease that was needed to provide the same stain removal performance X 100. The data are shown in Table VII.

TABLE VII

| Enzyme | Wash Performance |
|---|---|
| *B. lentus* subtilisin | 100 |
| N76D | 310 |
| N76D/S103A | 230 |
| N76D/V104I | 130 |
| N76D/I107V | 160 |
| N76D/S99D/S101R | 370 |
| N76D/S99D/S103A | 290 |
| N76D/S101R/S103A | 130 |
| N76D/S101R/V104I | 300 |

TABLE VII-continued

| Enzyme | Wash Performance |
|---|---|
| N76D/S103A/V104I | 320 |
| N76D/S103G/V104I | 160 |
| N76D/S103A/V104F | 210 |
| N76D/S103A/V104N | 110 |
| N76D/S103A/V104T | 170 |
| N76D/V104I/I107V | 210 |
| N76D/S99D/S101R/S103A | 220 |
| N76D/S99D/S101R/V104I | 140 |
| N76D/S101G/S103A/V104I | 170 |
| N76D/S101R/S103A/V104I | 150 |
| N76D/S103A/V104I/S105A | 170 |
| N76D/S103A/V104T/I107A | 120 |
| N76D/S103A/V104T/I107L | 110 |
| N76D/S103A/V104I/L126F | 110 |
| N76D/S103A/V104I/S128G | 280 |
| N76D/S103A/V104I/L135I | 160 |
| N76D/S103A/V104I/L135V | 160 |
| N76D/S103A/V104I/D197E | 170 |
| N76D/S103A/V104I/N204A | 160 |
| N76D/S103A/V104I/N204G | 150 |
| N76D/S103A/V104I/P210I | 470 |
| N76D/S103A/V104I/M222A | 100 |
| N76D/S103A/V104I/T260P | 280 |
| N76D/S103A/V104I/S265N | 190 |

EXAMPLE 7

Protease Stability in a Liquid Detergent Formulation

A comparison of protease stability toward inactivation in a liquid detergent formulation was made for Bacillus lentus subtilisin and it's variant enzyme N76D/S103A/V104I according to the procedure outlined herein. The detergent formulation used for the study was a commercially purchased bottle of Tide Ultra liquid lanudry detergent made in the USA by Procter & Gamble Company. Heat treatment of the detergent formulation was necessary to inactivate in-situ protease. This was accomplished by incubating the detergent at 96° C. for a period of 4.5 hours. Concentrated preparations of the B. lentus subtilisin and N76D/S103A/V104I variant, in the range of 20 grams/liter enzyme, were then added to the heat-treated Tide Ultra at room-temperature to a final 3concentratrion of 0.3 grams/liter enzyme in the detergent formulation. The heat-treated detergent with protease added was then incubated in a water bath thermostatted at 50° C. Aliquots were removed from the incubation tubes at 0, 24, 46, 76, and 112 hour time intervals and assayed for enzyme activity by addition to a 1 cm cuvette containing 1.2 mM of the synthetic peptide substrate suc-Ala-Ala-Pro-phe-p-nitroanilide dissolved in 0.1M tris-HCL buffer, pH 8.6, and thermostatted at 25° C. The initial linear reaction velocity was followed spectrophotometrically by monitoring the absorbance of the reaction product p-nitroaniline at 410 nm as a function of time. As shown in FIG. 10, the N76D/S103A/V104I variant was observed to have significantly greater stability towards inactivation than the native B. lentus enzyme. Estimated half-lives for inactivation in the Tide Ultra detergent formulation for the two enzymes, under the specified test conditions, are 45 hours for B. lentus subtilisin and 125 hours for the N76D/S103A/V104I variant.

Throughout this application reference is made to various amino acids by way of common one- and three-letter codes. Such codes are identified in Dale, J. W. (1989), *Molecular Genetics of Bacteria*, John Wiley & Sons, Ltd., Appendix B.

Although the preferred embodiments of the invention have been described above, it will be obvious to those skilled in the art to which the invention pertains, that, after understanding the invention as a whole, various changes and equivalent modifications may be made without departing from the scope of the invention as defined by the appended claims.

What is claimed is:

1. An isolated subtilisin variant having an amino acid sequence comprising a plurality of amino acid substitutions with a different amino acid, said substitutions made at:
   (a) position 76 in *Bacillus amyloliquefaciens* subtilisin;
   (b) position 107 in *Bacillus amyloliquefaciens* subtilisin wherein the different amino acid is selected from the group consisting of V, L, M, Y, G, E, F, T, S, A, N and I; and
   (c) the positions 103 and 104 in *Bacillus amyloliquefaciens* subtilisin;
   wherein said *Bacillus amyloliquefaciens* subtilisin has the amino acid sequence set forth in SEQ ID NO:7.

2. The isolated subtilisin of claim 1, wherein the different amino acid at position 107 is selected from the group consisting of V, L, Y, G, F, T, S, A and N.

* * * * *